United States Patent
Osypka

(10) Patent No.: US 10,456,168 B2
(45) Date of Patent: Oct. 29, 2019

(54) TRANSMYOCARDIAL INSERTION UNIT AND ITS USE

(71) Applicant: PETER OSYPKA STIFTUNG, Grenzach-Wyhlen (DE)

(72) Inventor: Peter Osypka, Grenzach-Wyhlen (DE)

(73) Assignee: Peter Osypka Stiftung, Grenzach-Wyhlen (DE)

( * ) Notice: Subject to any disclaimer, the term of this patent is extended or adjusted under 35 U.S.C. 154(b) by 173 days.

(21) Appl. No.: 15/517,088

(22) PCT Filed: Oct. 30, 2014

(86) PCT No.: PCT/EP2014/002915
§ 371 (c)(1),
(2) Date: Apr. 5, 2017

(87) PCT Pub. No.: WO2016/066180
PCT Pub. Date: May 6, 2016

(65) Prior Publication Data
US 2017/0296227 A1    Oct. 19, 2017

(51) Int. Cl.
*A61B 17/34* (2006.01)
*A61F 2/24* (2006.01)
(Continued)

(52) U.S. Cl.
CPC ........ *A61B 17/3423* (2013.01); *A61F 2/2487* (2013.01); *A61F 2/2493* (2013.01);
(Continued)

(58) Field of Classification Search
CPC .... A61F 2/2487; A61F 2/2493; A61F 2/2427; A61F 2/243; A61F 2/82; A61B 17/3423; A61B 2017/00252; A61B 2017/00867; A61B 2017/3425; A61B 2017/3441; A61B 2017/3488; A61B 17/34; A61M 1/101; A61M 1/1008; A61M 1/122; A61M 1/125; A61M 1/10; A61N 1/056; A61N 1/0587; A61N 1/05
See application file for complete search history.

(56) References Cited

U.S. PATENT DOCUMENTS

| 5,924,424 A | 7/1999 | Stevens et al. |
| 2002/0161378 A1 | 10/2002 | Downing |

(Continued)

FOREIGN PATENT DOCUMENTS

WO    WO-2008109408 A2    9/2008

OTHER PUBLICATIONS

International Search Report dated Jul. 2, 2015 in connection with priority Application No. PCT/EP2014/002915.
(Continued)

*Primary Examiner* — George J Ulsh
(74) *Attorney, Agent, or Firm* — Locke Lord LLP; Scott D. Wofsy

(57) ABSTRACT

An insertion device that allows gaining access to the left ventricle of the heart, via the tissue forming the wall of the right ventricle and via the ventricular septum, which includes a tubular shaft with a lumen extending there through, the shaft comprising distal, proximal and central sections, whereby the distal and proximal sections are disc-shaped extended thus forming each a double disc and whereby the central section links the distally placed double disc with the proximally placed double disc and whereby pressure valves are fixed inside the shaft preferably on its distal and proximal end.

8 Claims, 24 Drawing Sheets

(51) Int. Cl.
    *A61F 2/82*     (2013.01)
    *A61N 1/05*     (2006.01)
    *A61B 17/00*    (2006.01)
    *A61M 1/10*     (2006.01)
    *A61M 1/12*     (2006.01)

(52) U.S. Cl.
    CPC ...... *A61F 2/82* (2013.01); *A61B 2017/00252* (2013.01); *A61B 2017/00867* (2013.01); *A61B 2017/3425* (2013.01); *A61B 2017/3441* (2013.01); *A61B 2017/3488* (2013.01); *A61F 2/243* (2013.01); *A61F 2/2427* (2013.01); *A61M 1/101* (2013.01); *A61M 1/1008* (2014.02); *A61M 1/122* (2014.02); *A61M 1/125* (2014.02); *A61N 1/056* (2013.01); *A61N 1/0587* (2013.01)

(56) References Cited

U.S. PATENT DOCUMENTS

| | | |
|---|---|---|
| 2006/0074484 A1 | 4/2006 | Huber |
| 2008/0109069 A1 | 5/2008 | Coleman et al. |
| 2008/0147184 A1 | 6/2008 | Lattouf |
| 2009/0287240 A1 | 11/2009 | Yamatani |
| 2012/0130391 A1 | 5/2012 | Sundt, III et al. |
| 2013/0178908 A1 | 7/2013 | Huber |
| 2013/0331920 A1 | 12/2013 | Osypka |
| 2014/0039375 A1 | 2/2014 | Jimenez et al. |

OTHER PUBLICATIONS

Written Opinion dated May 6, 2016 in connection with priority Application No. PCT/EP2014/002915.

Fig. 1
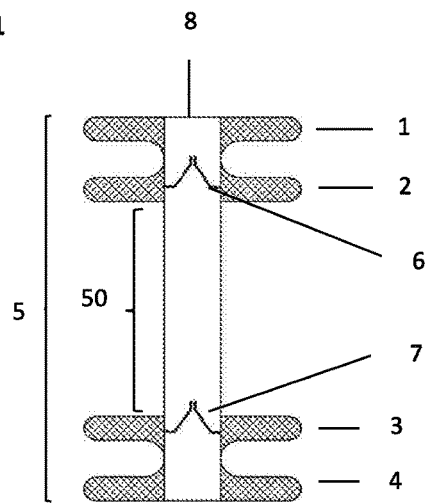
Fig. 1a
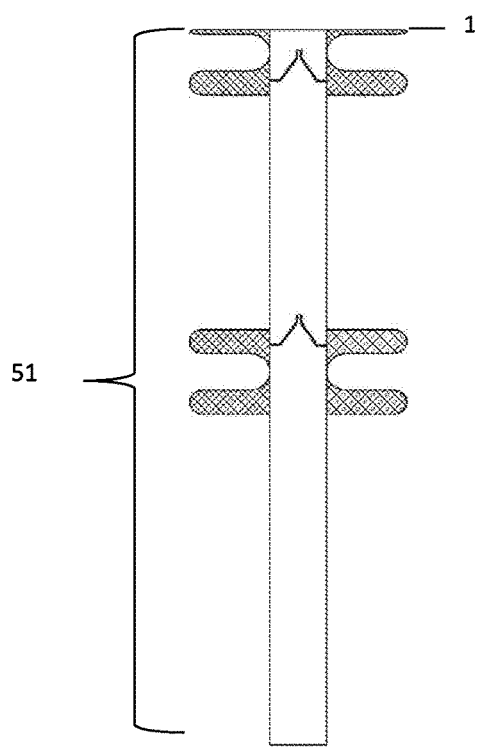
Fig. 1b
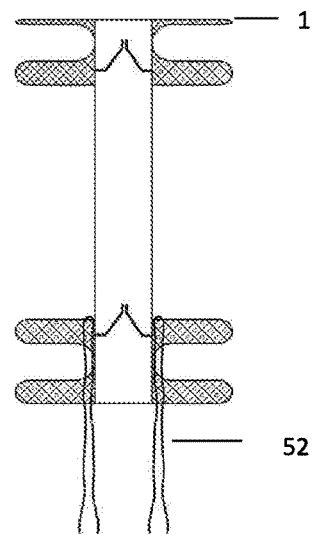
Fig. 1c

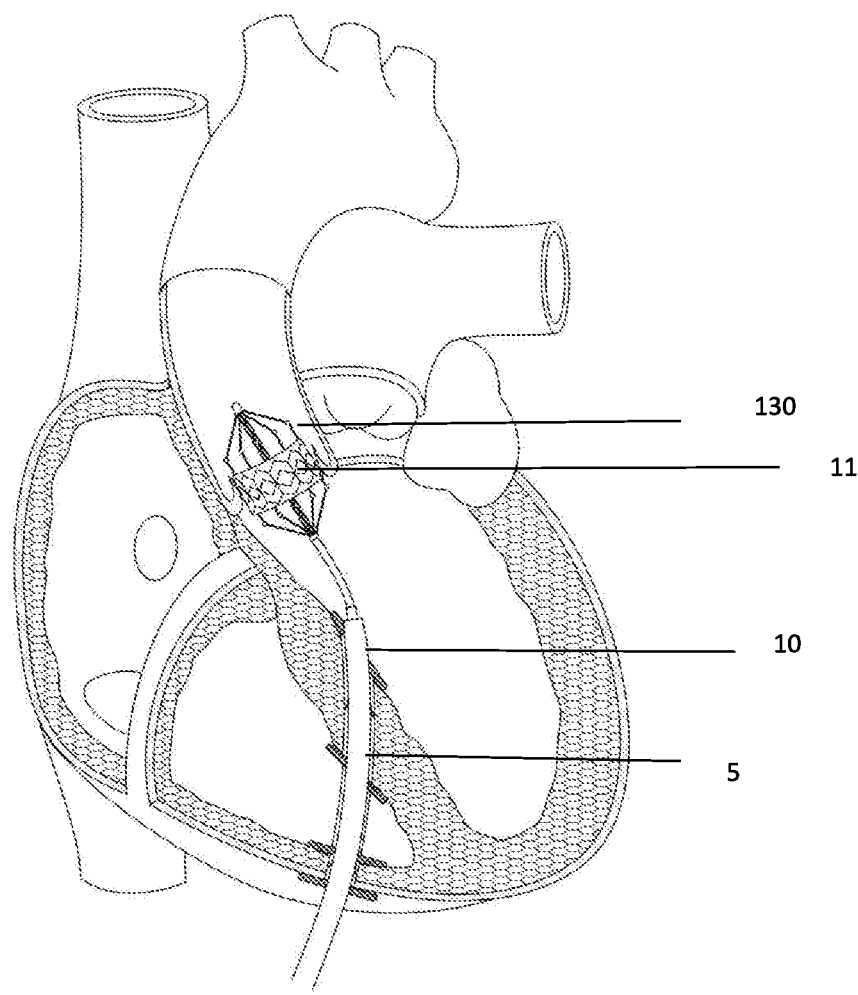
Fig. 22
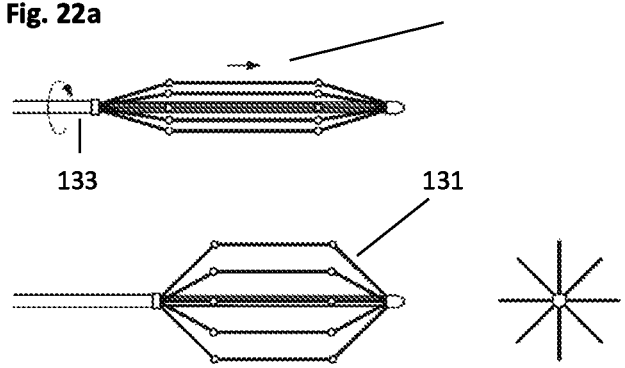
Fig. 22a
Fig. 22b

TRANSMYOCARDIAL INSERTION UNIT AND ITS USE

CROSS-REFERENCE TO RELATED APPLICATION

The subject application is a national stage application which claims priority to PCT Application No. PCT/EP2014/002915 filed Oct. 30, 2014.

BACKGROUND OF THE INVENTION

The invention relates to an insertion unit that for the first time allows gaining access to the left ventricle of the heart, via the tissue forming the wall of the right ventricle and via the ventricular septum.

Access to the left ventricle is a major concern both in the field of heart diagnostics and in heart therapy. Such an access would allow a great number of new therapies and diagnostic methods and/or would simplify the performing of well-known therapies and diagnostic methods. Therefore the invention also relates to devices using said insertion unit.

Examples for suitable devices are given below. The listed devices are by no means exhaustive.

Device for gaining access to all Chambers of the heart and to the abdominal region.
Device for stimulation and defibrillation of the heart.
Device for cardiac valve replacement and/or the dilatation of the replaced valves.
Device for repairing cardiac valves and for improving the mitral valve geometry.
Device for ventricle size reduction in case of a pathological ventricle enlargement.
Ventricular assist device (Heart pump)
Device for taking blood from the left ventricle and for supplying the heart muscle tissue with blood via the coronary arteries (Therapy of coronary stenosis, bypass operation).
Device for improving the myocardial blood flow.
Device for gaining access to the aortic valve by avoiding abrasion of calcified arterial plaque.
Device for monitoring post operation bypass blood flow.
Device suitable as a port to the heart chambers.
Device for mapping a heart chamber.
Device for treating atrial fibrillation with RF ablation.
Device for examining the inner walls of the heart chamber and of blood vessels
Device for repairing the ventricular septum (VSD) after pathological sudden rupture.
Device for gaining access to the pulmonary and aortic artery.
Device for transmitting cell material into the heart chambers
Device for monitoring the cardiac output by measuring impedance changes.

Access to the Left and Right Ventricle

The problem underlying the present invention is to gain access to the left ventricle without injuring the tissue forming the wall of the left ventricle. Moreover, the insertion of trocars, catheters, electrodes and implantable medical devices of all kind both into the left as well as into the right ventricle shall be made possible or shall be simplified.

The problem is solved by a new insertion unit allowing the above required access to the left ventricle. The access to the left ventricle via the muscle tissue of the right ventricle and the ventricular septum is particularly desirable because the pressure in the right ventricle is lower than in the left ventricle. Moreover the muscle tissue that makes up the wall of the left ventricle is about three times thicker than that of the right ventricle.

The invention thus relates to an insertion unit comprising a tubular shaft (FIG. 1) (5) with a lumen (8) extending there through, said shaft comprising distal, proximal and central sections, whereby the distal and proximal sections are disc-shaped extended thus forming each a double disc (1), (2) resp. (3) (4) and whereby the central section (50) links the distally placed double disc (1), (2) with the proximally placed double disc (3),(4), and whereby pressure valve (6) resp. (7) are fixed inside the shaft preferably on its distal and proximal end.

The used expression "disc-shaped" also includes related structures like umbrella-shaped, discus-shaped or ellipsoid-shaped. The double disc serves as a fixation device like an occlusion member.

The disc-shaped extensions (1), (2), (3) and (4) have a larger diameter than the tubular shaft (5), approximately five times to fifteen times greater.

The distally placed double disc (1), (2) is suitable for being implanted in the ventricular septum. The proximally placed double disc (3), (4) is suitable for being implanted in the heart muscle tissue of the right ventricle.

The double discs serve for placing and fixing the insertion unit into the ventricular septum resp. into the muscle tissue of the right ventricle. Due to its disc-shaped extensions, the insertion unit remains in position after its implantation and sliding is prevented.

The dimensions of the tubular shaft (5) are adapted to the anatomical structure between left and right ventricle.

For accessing the right ventricle the central section (50) has a lateral opening (Y-piece with valve). An access to the right ventricle or to the abdomen can also be achieved using an insertion unit comprising only double disc (1), (2) and a pressure valve fixed therein.

The present insertion unit consists of a biocompatible and flexible material. Each biocompatible material is suitable that may form a tubular shaft with disc-shaped extensions. It must be possible to fix at least two pressure valves, e.g. silicone valves, inside the shaft. The insertion unit must be foldable so that it can be inserted by means of a trocar.

Suitable materials are for example polymeric materials like silicone or polyurethane; metals like stainless steel, nickel-alloy MP35N or shape-memory materials like nitinol wires, nitinol strands, nitinol threads. The nitinol wires, strands and threads may be coated with polymeric material. Furthermore, shape-memory plastic threads, nitinol wires coated with other metals, e.g. nitinol wires coated with gold or platinum may also be suitable.

In a preferred embodiment the insertion unit is made of braided wires of shape-memory material (preferably nitinol) said wires and thus the whole insertion unit may form a common electrical pole, if connected to an Implantable Cardiac Defibrillator (ICD).

If the insertion unit is made of braided nitinol wires a tubular shaft is first braided, said shaft being deformed by heat or pressing in such a way that it forms disc-shaped extensions (1), (2), (3) and (4). These discs can be formed by braiding a single braid or a double braid lying on top of each other.

Shaft (5) of the insertion unit may completely or partly be coated with biocompatible polymeric material, e.g. silicone. Such a coating prevents blood intrusion into the inner braided part. The coating can be inside or outside. Preferably the central section (50) of the shaft is coated with biocompatible polymeric material. The term "coated with biocompatible polymeric material" also includes a polymer tube being pulled over the braided central section.

The proximal wire ends of the braided tubular shaft can be fixed by a sleeve or holder that has an opening too, so that lumen (8) is continuous.

However, the insertion unit can also be braided in two parts and be welded in the central section. Such a direct welding is described in WO2012095314.

The insertion unit can also consist of two pieces. In a two-piece design the central section (50) of the tubular shaft (5) is made from another material or has another design than the distal and proximal sections. In one embodiment the central section (50) of the tubular shaft is completely or partly coil shaped, said coil serving as spring. Said coil may be coated inside and/or outside with silicone or with other suitable biocompatible material or the coil is covered with a silicone tube.

The lumen (8) extends through the whole tubular shaft of the insertion unit in axial direction. At least two pressure valves are fixed inside the shaft preferably on its distal and proximal end. The distally placed pressure valve (6) is important in order to prevent the blood flow from the left to the right ventricle. The proximally placed pressure valve is important to prevent bleeding through the puncture of the right ventricle. The pressure valves are preferable silicone valves that are commercially available in many shapes and sizes. Suitable valves can be bought from the company Minivalve Int. B.V. for instance.

The tubular shaft (5) may be longitudinally extended thus forming an extended shaft (51). Said extended shaft may also be coated with a biocompatible polymeric material. The extended shaft may also be coil shaped similar to the central section.

The thus extended shaft comprises a further double disc (53),(54) with pressure valve (55) at its proximal end. The thus obtained insertion unit comprises three double discs being linked by the central section resp. the extended section of the shaft. The thus obtained insertion unit is suitable for gaining access to the left ventricle via the abdomen, the right ventricle and the ventricular septum.

The insertion unit may be a permanent implant. It can grow into the surrounding tissue like already known septal Occluder.

If desired, one or several sensors e.g. pressure sensors can additionally be fixed inside the shaft of the insertion unit.

In one embodiment, the insertion unit consists completely or partly of biocompatible synthetic material like silicone or polyurethane.

In another embodiment, the insertion unit consists completely or partly of a metal coil.

In a preferred embodiment the whole insertion unit is braided of nitinol wires. The insertion unit thus comprises a braided tubular shaft (5) of nitinol wires with a lumen (8) extending there through, said shaft comprising distal, proximal and central sections, whereby the distal and proximal sections are disc-shaped extended thus forming each a double disc (1), (2) resp. (3) (4) and whereby the central section (50) that links the distally placed double disc (1), (2) with the proximally placed double disc (3),(4) is coated with a biocompatible polymeric material, and whereby pressure valve (6) resp. (7) are fixed inside the shaft on its distal and proximal end.

Surgical threads may be woven into the proximal braiding. The threads can be tied together with a knot and serve as additional fixing of the double disc and as sealing of the muscle tissue forming the heart wall.

The insertion unit according to the invention can be used to insert a number of medical devices. Therefore the aim of the present invention is also to make devices available that are suitable for carrying out new therapies and diagnostic methods and/or that simplify carrying out well-known therapies and diagnostic methods. Examples of such devices are: Devices for Stimulation and Defibrillation of the Heart (FIG. 6,7,8,9)

If the stimulation/defibrillation of the right and/or left ventricle is desired, the insertion unit according to the invention, which in this case must consist of a conducting material (e.g. nitinol), is connected to an ICD (Implantable Cardiac Defibrillator) to form one of the defibrillation electrodes or to form an indifferent electrode pole. The other stimulation or defibrillation poles can be standard implantable electrodes.

As shown in FIG. 8 the second defibrillation electrode can be an occlusion device placed in the atrial septum. The metal frame of the artificial valve may also serve as second defibrillation electrode (FIG. 9). The standard stimulation electrode or pace-sense electrode consisting of a lead provided with a pole at its distal end portion is inserted through the shaft of the insertion unit and guided to the left ventricle, fixed and connected to an ICD or pacemaker (FIG. 6). The lead runs inside the shaft.

If biventricular stimulation is desired, another stimulation electrode is inserted through the shaft of the insertion unit which in this case has a lateral opening. The electrode is guided to the right ventricle, fixed and connected to an ICD or pacemaker (FIG. 7). The number of stimulation electrodes is not limited. Depending of the number and the position of the pacing leads, one can use it as a one chamber pacing system or a biventricular stimulation system.

Every known unipolar or bipolar stimulation electrode or ICD electrode can be used. The distal pole of the electrode can be a screw type, for instance.

For the first time, biventricular stimulation is possible without the need of introducing the electrodes via the coronary sinus vein. The difficult positioning and fixation within the coronary sinus can be avoided. It will therefore reduce the number of so called "non responder".

Device for Cardiac Valve Replacement and/or the Dilation of the Replaced Valve (FIG. 3, 4, 22)

The inventive insertion unit is combined with a trocar to push in a cardiac valve prosthesis. Standard procedure known as TAVI (Trans catheter Aortic Valve Implantation) is carried out. A catheter (trocar) is inserted through the shaft of the insertion unit. Before the new Aortic Valve can be placed, the present old valve has to be dilated with a balloon catheter in order to gain space for the new valve. A cardiac valve prosthesis is pushed through the trocar. The artificial valve mounted on a metal frame is fixed on a balloon and will be positioned directly inside the diseased valve. The standard TAVI procedure is normally carried out by entering through the tip of the left ventricle (the apex). Closing the opening of the left ventricle, which has to be done when using the common left ventricular approach, is a big surgical problem. The tissue around the opening of the heart is especially for old patients very soft and therefore very sensitive to any suture manipulation. With the inventive insertion unit one can eliminate this problem by entering the heart chamber through the right ventricle. If required the balloon is inserted via a guide wire with a distal filter to protect the brain arteries in order to avoid possible abrasion of calcified arterial plaque.

In order to open a narrow heart valve balloon valvotomy is commonly performed. Instead of a balloon a balloon-free dilatation catheter can be used having at its distal end a cage like expander having elongated expanding element as shown in FIG. 22.

Device for Ventricle Size Reduction (FIG. 11)

In order to reduce the ventricle size in case of a pathological ventricle enlargement, the insertion unit according to the invention is modified by reducing the number of distally placed discs (1), (2) to one disc (1), The distally placed disc (1) has fixation hooks (60) that can be fixed in the muscle tissue forming the wall of the left ventricle resp. in the ventricular septum. The central section (50) between the fixed disc (1) and the braided double discs (3) and (4) is elastic, similar to a spring. In FIG. 11 the central section is formed as a spring (61).

Device for Improving or Increasing the Cardiac Output
Electromechanical Device (FIG. 5)

A heart pump is inserted through the shaft of the inventive insertion unit and guided to the left ventricle and further to the ascending aorta. Suitable heart pumps are commercially available; for example the Impella®-Pump Pneumatic Device (FIG. 17)

A pneumatic device is placed into an artificial blood vessel system, said system being combined with the present insertion unit as described in the following paragraph. A blood pump is placed into the artificial blood vessel in such a way that blood is sucked from the left ventricle and transported into the aorta (FIG. 17). This would provide benefits especially to patients waiting for a heart transplant.

Device for Taking Blood from the Left Ventricle and for Supplying the Heart Muscle Tissue with Blood Via the Coronary Arteries (FIG. 13, 14)

The combination of the inventive insertion unit with an artificial blood vessel system provides a device allowing a new and simplified bypass surgical technique.

The artificial blood vessel system consists of an unbranched or branched tube. One end of said tube is placed and fixed (e.g. by bonding) within the shaft of the insertion unit. The other end of the tube can be arranged around the heart. The tube is variable in length and shape so that the artificial blood vessel can be put around the heart (around the ventricles and/or the atria) partly or completely or can be guided to other organs in the abdomen as well. Every anastomosis typically used in surgery can be considered for fixing the artificial blood vessel on the heart tissue.

The artificial blood vessel has one or more small branches being connectable to a coronary artery and thus serving as bypass. The small branches are put over the blocked coronary artery and are sewed or bonded below the stenosis. These small branches serving as bypass have a smaller diameter than the tube of the artificial blood vessel system.

For treating coronary stenosis the artificial blood vessel is fixed on the heart tissue. After puncturing said artificial blood vessel the blocked coronary arteries are supplied with blood. The stenosis can thus be treated without removing a leg vein for instance. Moreover, the aorta does not have to be punctured. The operation is done without using a heart-lung-machine.

Suitable artificial blood vessels must consist of elastic biocompatible material, e.g. polytetrafluoroethylene (brand name Gore Tex) or polyester. Specialists are familiar with suitable materials and artificial blood vessels are commercially available (e.g. the product Dardik Biograft from the company Meadox Medical Inc. or products from the company Boston Scientific). Generally, each biocompatible elastic material is suitable.

Improvement of the Myocardial Blood Flow (FIG. 14)

The tube member of the artificial blood vessel may have a number of cannula- or thorn-like branches being arranged around the vessel and extending up into the myocardium like an injection needle in order to supply the myocardium with blood. Furthermore the formation of coronary vessels is activated.

Device for Taking Blood from the Left Ventricle and for the Simultaneous Stimulation and Defibrillation (FIG. 15, 16)

The above mentioned device combining the inventive insertion unit with an artificial blood vessel system can be equipped with implantable pacemaker leads so this unit is also suitable for stimulation and defibrillation.

As described above, the insertion unit, which in this case must consist of a conducting material (e.g. nitinol), is connected with an ICD to form one of the defibrillation electrodes or to form an indifferent electrode pole. At least one pacemaker lead is inserted via said insertion unit and guided to the left resp. right ventricle in order to establish a stimulation unit. By wrapping parts of the artificial blood vessel with a metallic coil a defibrillation electrode is formed. The defibrillation shock is given between the insertion unit and the metallic coil each being connected to an ICD.

Device for Monitoring Post Operated Bypass Blood Flow (FIG. 16)

The above mentioned device combining the inventive insertion unit with an artificial blood vessel system can be equipped with electrode poles or sensors that are in contact with a measuring unit and are suitable to monitor the blood flow in the bypass, e.g. by measuring the change of the electrical impedance between two sensors. The records can be saved and transferred by telemetry, if required. Any reduced blood flow is displayed immediately so that remedial action can be taken rapidly.

Examples for sensors are: ultrasonic sensors and/or flow sensors for controlling the blood flow; pressure sensors for controlling the blood pressure.

Device being Suitable as Port Catheter (FIG. 10)

The insertion unit according to the invention can also be connected with a subcutaneous port. For this purpose, the insertion unit is connected with the port chamber via flexible tubing. Medicine can thus be given into the ventricle via said port or blood samples can be taken as well.

Device for Inspecting the Inner Part of the Heart (FIG. 18)

Catheter type endoscopes with a video chip at the tip within a transparent balloon can be inserted through the shaft of the inventive insertion unit and guided to the inner part of the heart. By inflating the transparent balloon with CO2 gas or saline solution and pushing it to the desired area, the endoscope can inspect visually the inner parts of the heart.

Device for RF Ablation of Heart Tissue

One or several electrodes connected with a RF generator can be inserted through the shaft of the inventive insertion unit and guided to the left and/or right heart chambers to start the ablation procedure.

Device for Mapping a Heart Chamber

A steerable catheter with one or several mapping electrodes connected to a recording device can be inserted through the shaft of the inventive insertion unit and guided to the left and/or right heart chamber.

Device for Repairing the Ventricular Septum Defect (VSD) after Pathological Sudden Rupture (FIG. 19)

The immediate surgical closing of a sudden rupture of the ventricular septum is in most cases not possible, due to the tissue characteristic after the rupture.

A closing device is obtained by using enlarged braided occlusion discs (1), (2) as clamping means for closing ventricular septal defects or rupture. By adding some new tissue obtained by tissue engineering and/or nanotechnology developed or own harvested tissue material, the healing process could be improved.

Device for Gaining Access to the Pulmonary Artery and Right Atrium

The inventive insertion unit allows gaining access to the pulmonary artery and right atrium via the right ventricle.

Device for Transmitting Cell Material into the Heart Chambers

The inventive insertion unit allows transmitting cell material into the heart chambers. A carrier containing said cell material is inserted through the shaft of the inventive insertion unit and guided to the heart chambers.

Device for Improving the Mitral Valve Geometry by Reducing the Valve Area. (FIG. 20)

In order to reduce the amount of blood leaking backwards, the two leaflets of the mitral valve are—in known methods—partially clipped or sewn together. The inventive insertion unit allows a new mitral valve repair approach by using the insertion unit to insert a device for pushing anchors. A suitable device for pushing anchors is described in WO2007079952 corresponding to US20090012557. Instead of the presently used "clipping" procedure, or the presently used suture methods with one or more knots with the sutures, the new approach using the insertion unit results in reducing the size of the mitral (cardiac) valve as desired in a simplified procedure.

Device for Calculating and Monitoring the Cardiac Output. (FIG. 21)

A first electrical impedance measuring electrodes is inserted through the shaft of the insertion unit and fixed in the tissue of the left ventricle. A second impedance measuring electrodes is inserted through the shaft of the insertion unit and fixed in the tissue of the right ventricle. Both electrodes are connected to an electrical impedance measuring device thus forming an impedance measurement circuit. The cardiac impedance changes between systole and diastole. Those data are the basis to determine the stroke volume of the heart. An apparatus and a method for determining an approximate value for the stroke volume and the cardiac output of a person's heart is described in U.S. Pat. No. 6,511,438.

The present invention also refers to therapeutic and diagnostic methods that can be carried out with the above mentioned devices.

Many aspects of the invention can be better understood with reference to the following figures showing the insertion unit in detail and number devices using the insertion device.

The reference numbers represent:

| | |
|---|---|
| A | Aorta |
| CV | Coronary vein |
| LV | left ventricle |
| RV | right ventricle |
| RF | radio frequency |
| ICD | (Implantable Cardiac Defibrillator) |
| (1, 2), (3, 4), (53, 54) | double discs |
| 5 | tubular shaft |
| 6, 7, 55 | pressure valves |
| 8 | lumen |
| 9 | pressure sensor |
| 10 | catheter (trocar) |
| 11 | metal frame of the artificial valve |
| 12 | balloon |
| 13 | heart pump |
| 14, 15 | stimulation electrodes, pace sense electrodes (lead and pole) |
| 16, 17 | electrode lead |
| 18, 19 | impedance measuring electrodes |
| 20, 21, 22, 23 | defibrillation electrodes |
| 24, 25, 26, 27, 28, 31 | electrical connection line |
| 30 | pump motor |
| 31 | propeller shaft |
| 32 | electrical impedance measurement unit |
| 33 | pump control unit |
| 34 | pacemaker |
| 40 | port chamber |
| 41 | port catheter |
| 50 | central section of the tubular shaft |
| 51 | extended tubular shaft |
| 52 | surgical threads |
| 60 | fixing hook |
| 61, 62 | spring |
| 63 | sleeve |
| 70 | abdomen (abdominal wall, chest wall) |
| 80 | artificial blood vessel, tube member |
| 81 | small vessel branch, |
| 82 | cannula-like branches |
| 83 | tube member branch |
| 90 | electrode pole |
| 91 | control electrode (sensor) |
| 92, 93 | pair of electrodes, pair of sensors |
| 100 | hose pump |
| 110 | endoscope |
| 111 | endoscope-balloon |
| 112 | endoscope shaft |
| 113 | endo scope tip |
| 120 | new tissue material |
| 121 | anchor pusher |
| 122 | feed catheter for anchor pusher |
| 130 | dilation catheter |
| 131 | elongated expanding elements |

BRIEF DESCRIPTION OF THE DRAWINGS

FIG. 1 shows the insertion unit according to the invention.

In FIG. 1a all the discs (1),(2),(3),(4) are formed by braiding two discs braids that lie on top of each other. In FIGS. 1b and 1c one of the discs (disc 1) is formed by braiding only one disc braid.

FIG. 1a shows the insertion unit consisting of a tubular shaft (5) braided of nitinol wire. The shaft has a lumen (8) extending through the whole shaft in axial direction. The central section (50) links the distally placed double discs (1), (2) with the proximal placed double discs (3), (4). Pressure valves (6) rep. (7) is fixed inside the shaft on its distal and proximal end.

FIG. 1b shows a longitudinally extended tubular shaft (51).

In FIG. 1c surgical threads (52) are woven into the braiding proximally. The threads can be tied with a knot together and serve as additional fixing of the proximal double disc and as sealing of the heart-wall tissue.

The proximal wire ends of the braided double discs (1) (2) resp. (3), (4) are fixed by a sleeve (63) that has an opening too, so that lumen (8) is continuous.

The following figures show the insertion unit implanted in the heart.

Figure 1D:
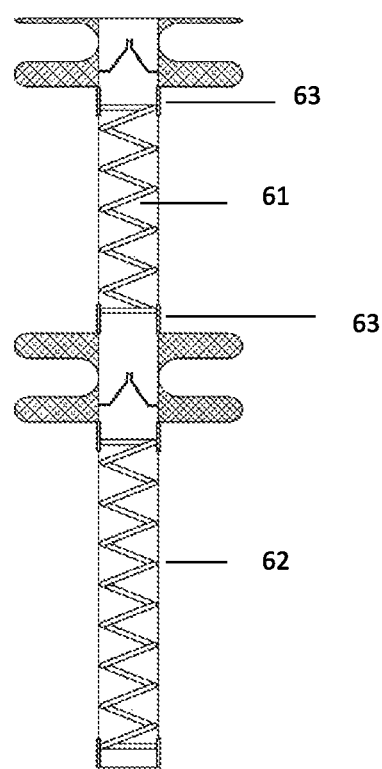
FIG. 1d shows an insertion unit where the central section (50) of the tubular shaft (5) has another design than the distal and proximal sections. The central section (50) of the tubular shaft is coil shaped, said coil (61) serving as spring. Said coil is covered with a silicone tube. The extended section is also coil shaped (62).
Figure 2:
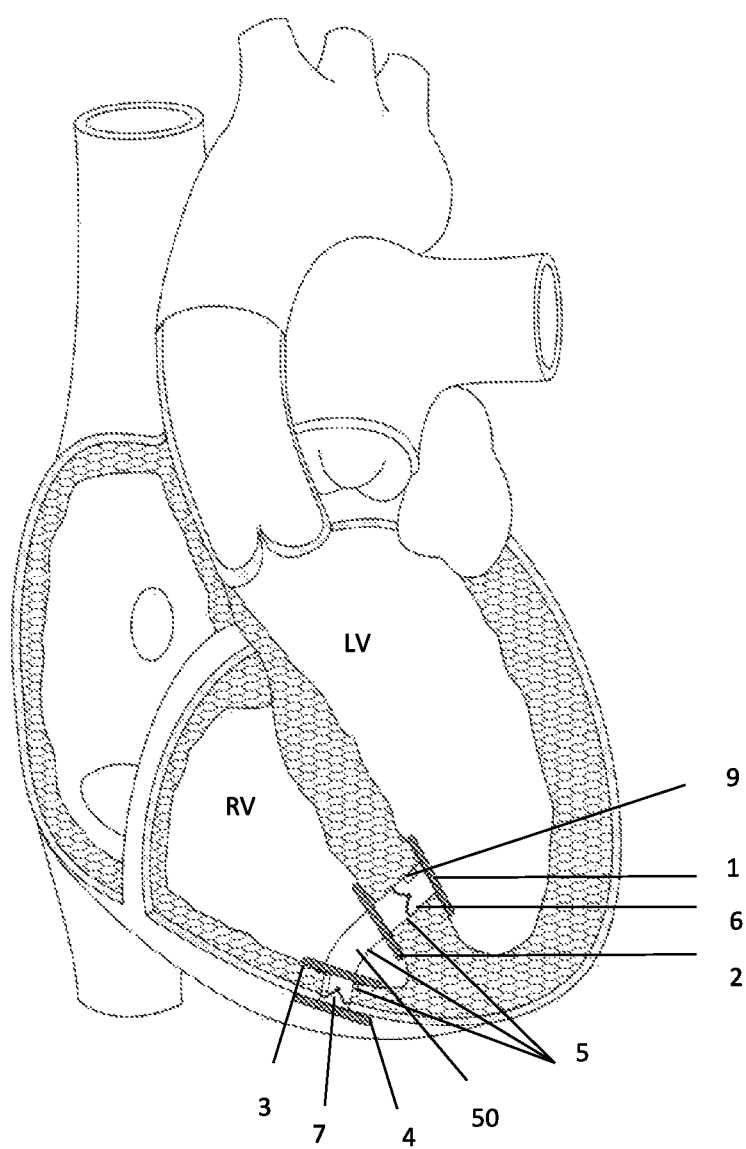

FIG. 2 shows the insertion unit implanted in the heart chambers. The braided double discs (1), (2) are implanted in the ventricular septum. The braided double discs (3), (4) are implanted in the tissue forming the heart wall of the right ventricle. Double disc (1), (2) is linked to double disc (3), (4) by the central section (50) of the shaft (5). Valve (6) prevents the blood flow from the left to the right ventricle. Valve (7) prevents bleeding through the puncture of the right ventricle. A pressure sensor (9) can be fixed inside the shaft at its distal end for measuring the left ventricular pressure. The pressure sensor can either transfer the data according to the RFID principle, or can transfer the data to a measurement unit. If required, the data can be saved.

Figure 3:
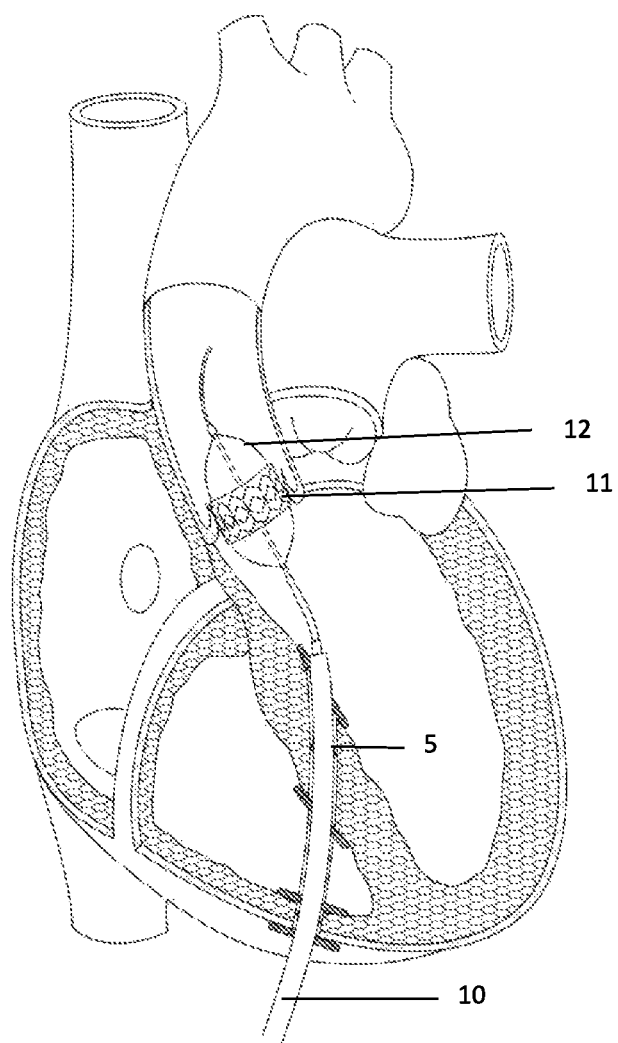
Figure 4:
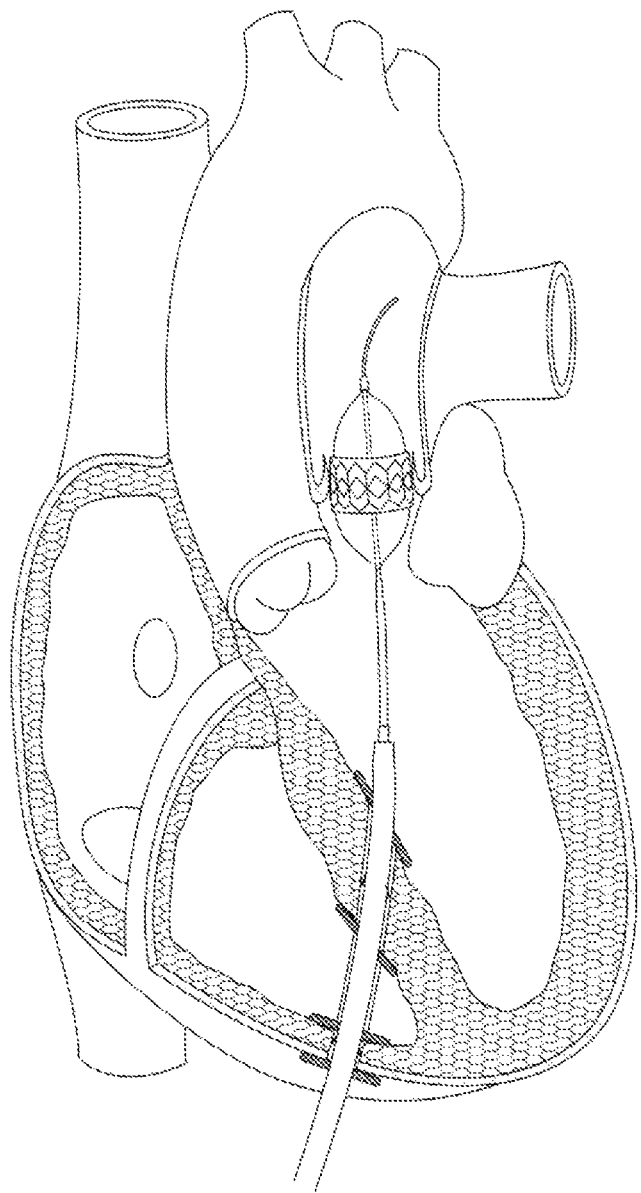

FIG. 3 and FIG. 4 show a device for the cardiac valve replacement and/or the dilation of the replaced valves. A catheter (trocar) (10) is inserted through shaft (5) of the inventive insertion unit and guided to the left ventricle. Cardiac valve prosthesis comprising a metal frame (11) positioned on a balloon (12) is pushed through said catheter and guided to the aortic valve to be replaced. FIG. 4 shows the possible replacement of the mitral valve.

Figure 5:
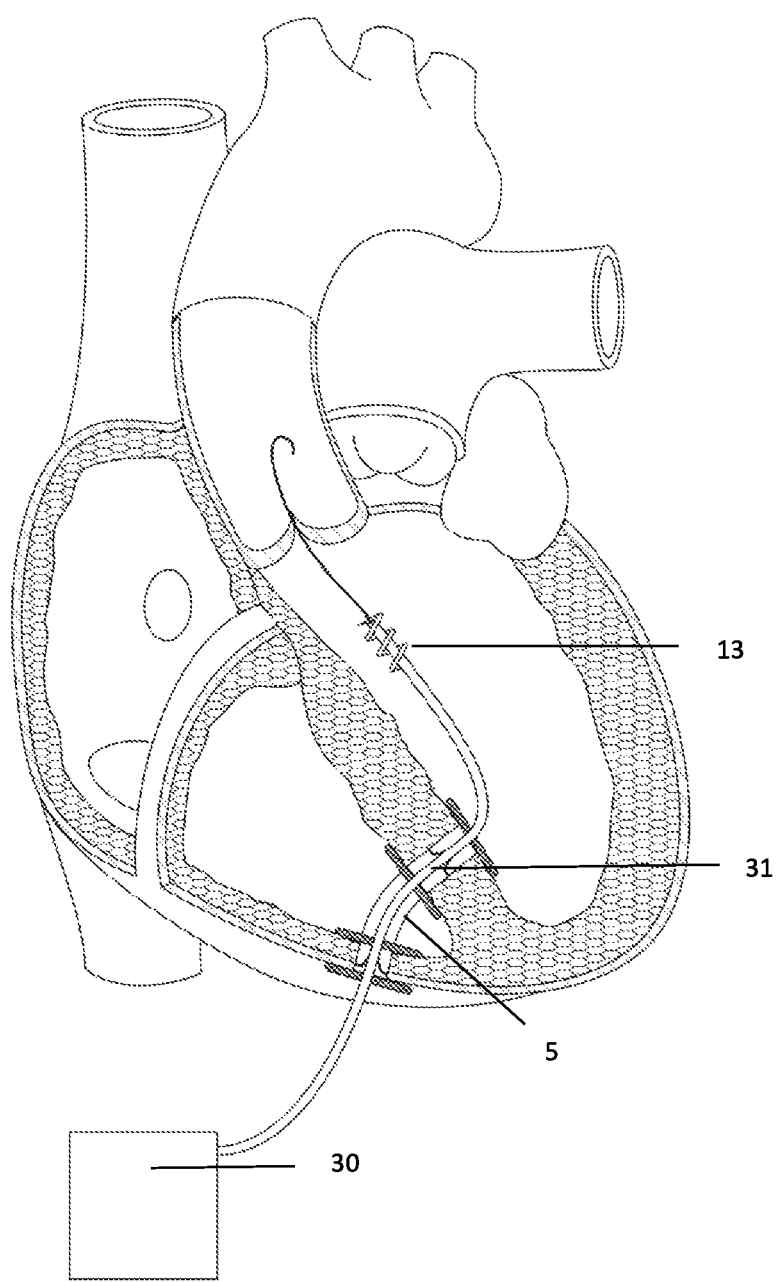

FIG. 5 shows a device supporting the cardiac blood flow output consisting of the inventive insertion unit and heart pump (13) being inserted through the shaft (5) of the insertion unit and guided via the left ventricle to the ascending aorta. The device pumps blood from the left ventricle into the ascending aorta. The heart pump (13) is driven by a motor (30) to which the propeller shaft is connected, said propeller shaft (31) running inside the insertion unit (5).

Figure 6:
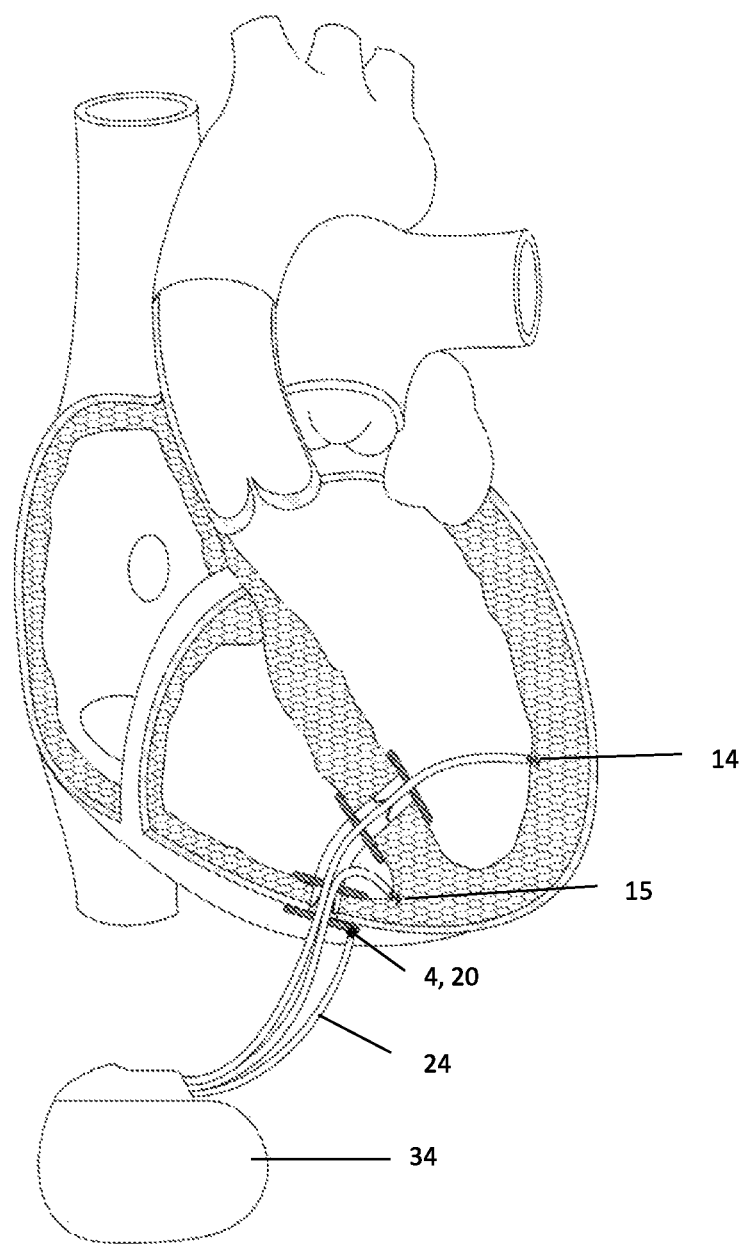

FIG. 6 shows a biventricular stimulation device. Depending of the number and the position of the pacing leads, one can use it as a one chamber pacing system or a biventricular stimulation system. The stimulation electrodes (screw tip) (14) from the left ventricle and (15) from the right ventricle are connected to the pacemaker (34). The electrical connection line (24) leads to the proximally placed disc (4) of the insertion unit. The insertion unit is braided of nitinol wires and the whole insertion unit with the discs 1,2,3,4, thus serves as the indifferent pole (20).

Figure 7:
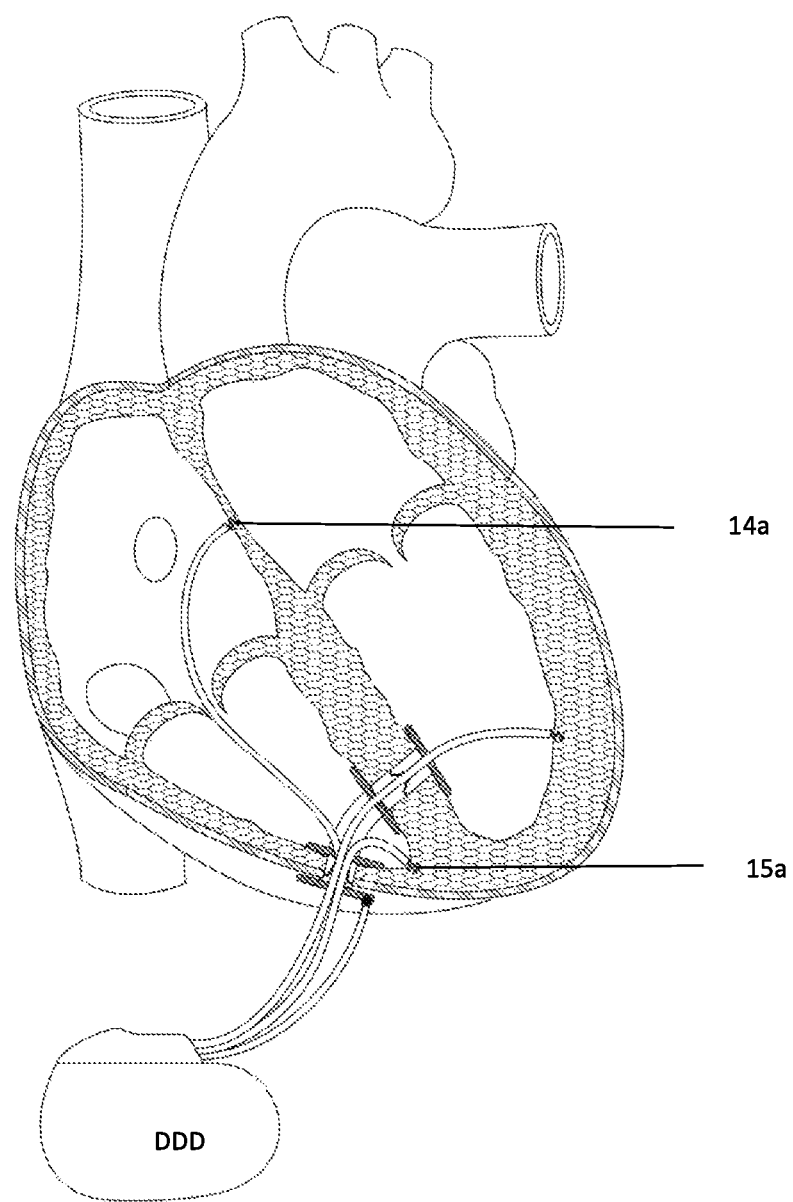

FIG. 7 shows the inventive insertion unit with a DDD stimulation device. The position of one screw tip lead (14a) is within the right atrium, the other electrode (15a) is fixed within the right ventricle.

The following FIGS. 8, 9, 10 and 15 show a stimulation/defibrillation device.

Figure 8:
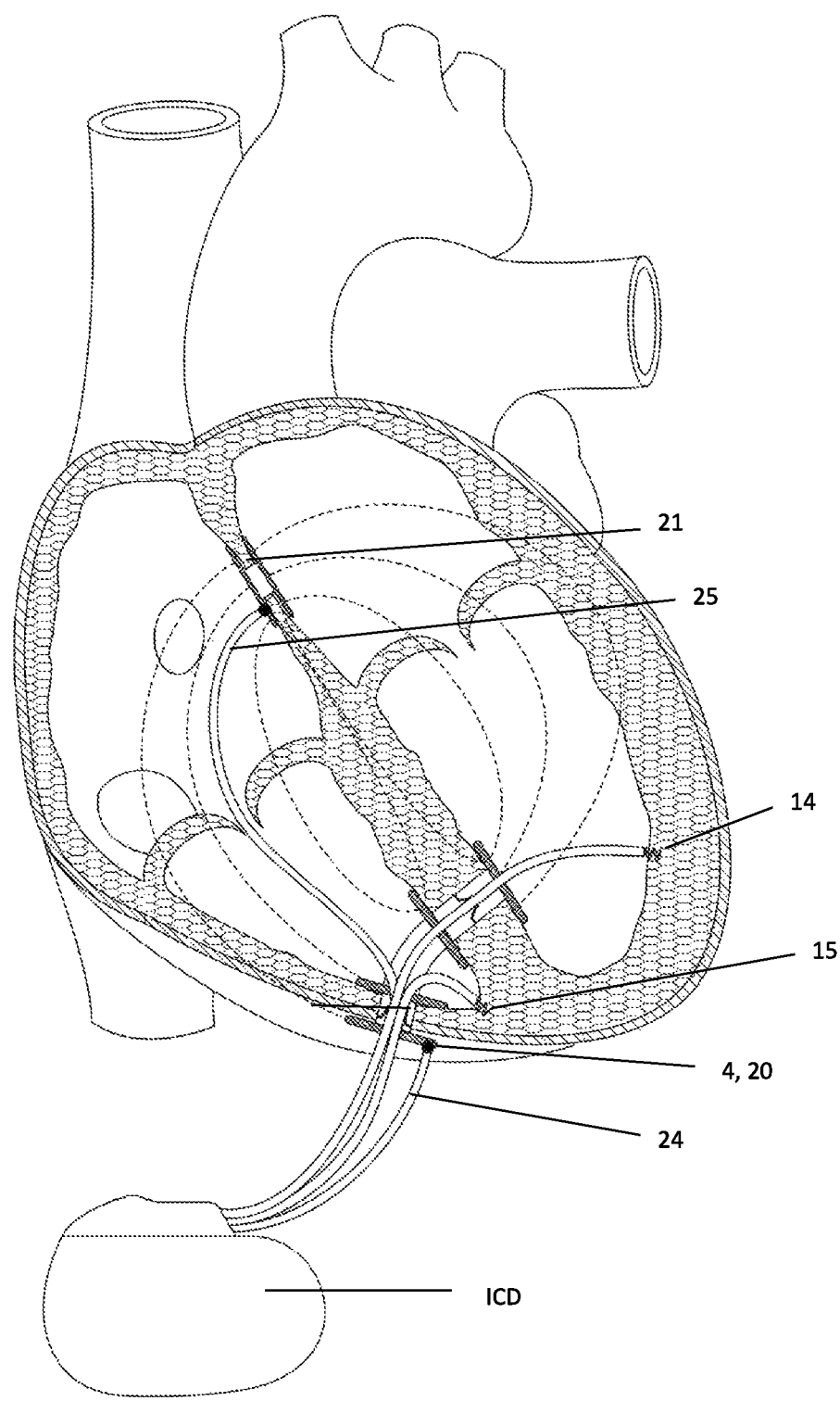

FIG. 8 shows a device for stimulation and defibrillation. In FIG. 8 an occluder implanted in the atrial septum, is connected to the ICD via electrical connection line (25). The occluder serves as defibrillation electrode (21). The electrical connection line (24) leads to the ICD. The insertion unit is braided of nitinol wires and the whole unit with the discs 1,2,3,4, thus serves as the second defibrillation electrode (20). The shock is given between the defibrillation electrodes (20) and (21). The stimulation and sensing electrodes (14) and (15) each consisting of a lead provided with a pole at its distal end are also connected to the ICD.

The field strength distribution is marked. One can see a homogenous electrical field over the right and over the left ventricle which may reduce the necessary defibrillation shock energy.

Figure 9A:
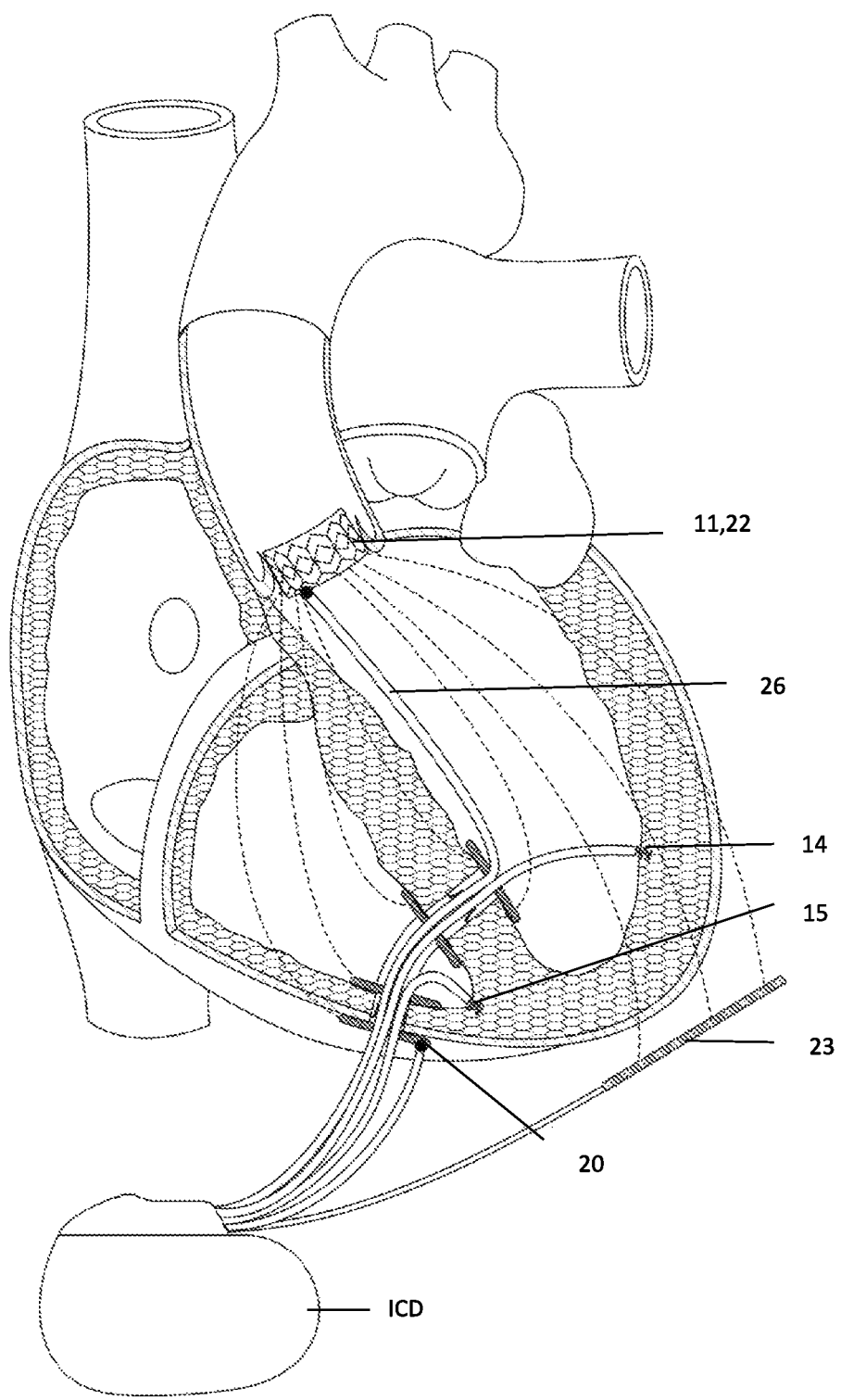

FIG. 9a also shows another possible device for stimulation and defibrillation for patients which have already an implanted artificial valve.

In FIG. 9a the metal frame (11) of the artificial valve is connected to the ICD via electrical connection line (26). The valve prosthesis thus forms one of the defibrillation electrodes (22). The shock is applied between the defibrillation electrodes (20) (disc (1), (2), (3), (4) of the insertion unit and the metal frame (11) forming the electrode (22). The stimulation electrodes (14) and (15) are connected to the ICD as described above.

If desired, a coil-shaped pole (23) may also serve as second defibrillation electrode. The coil is placed below the cardiac apex and is connected to the ICD. The shock is applied between the valve prosthesis (22) and the coil (23) or between the valve prosthesis (22) and the coil and parallel to the insertion unit (20).

The field strength distribution is marked. One can see a homogenous electrical field over the right and over the left ventricle.

Figure 9B:
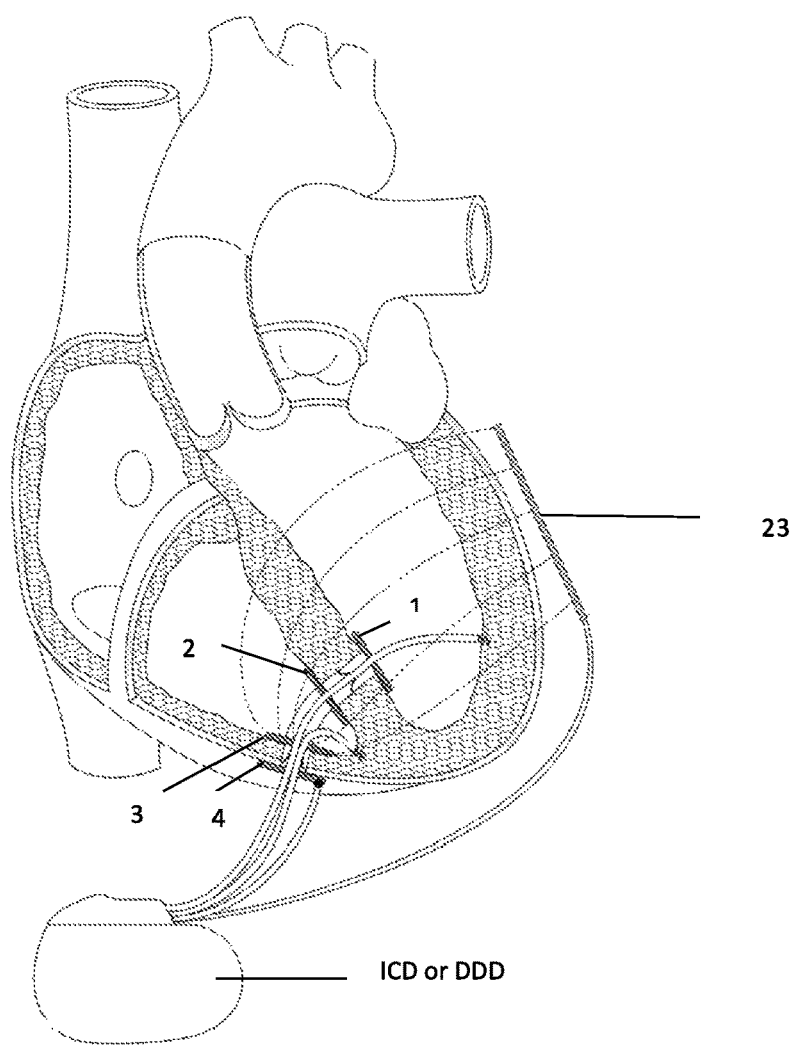
Figure 9B:
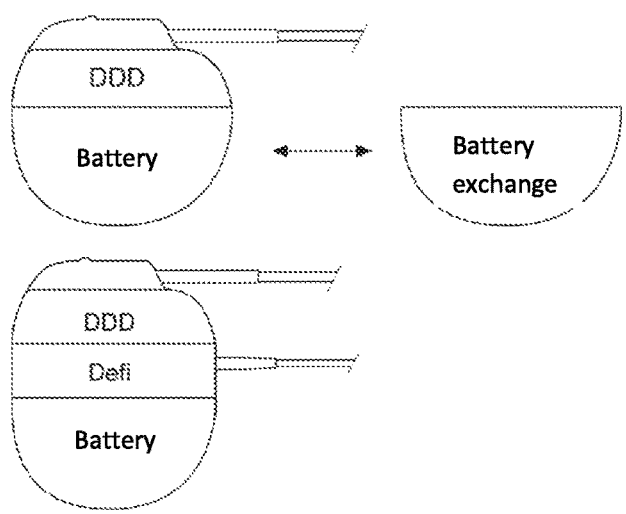

FIG. 9b also shows another possible device for stimulation and defibrillation of the heart. One of the defibrillation poles is a flexible coil (23), which is placed on left side of the heart. The shock is given between insertion unit serving as the defibrillation electrode (20) and (23). The ICD is implanted within the abdomen. The battery of the ICD can be exchanged without disconnecting the electrical circuitry from the electrodes. Thus the special program for pacing and defibrillation of those patients can be saved and continued to use without any new programming. A further advantage is that the capacity of the battery can be enlarged and the exchange of the battery can be done by any surgeon without any special experience in ICDs.

Figure 10:
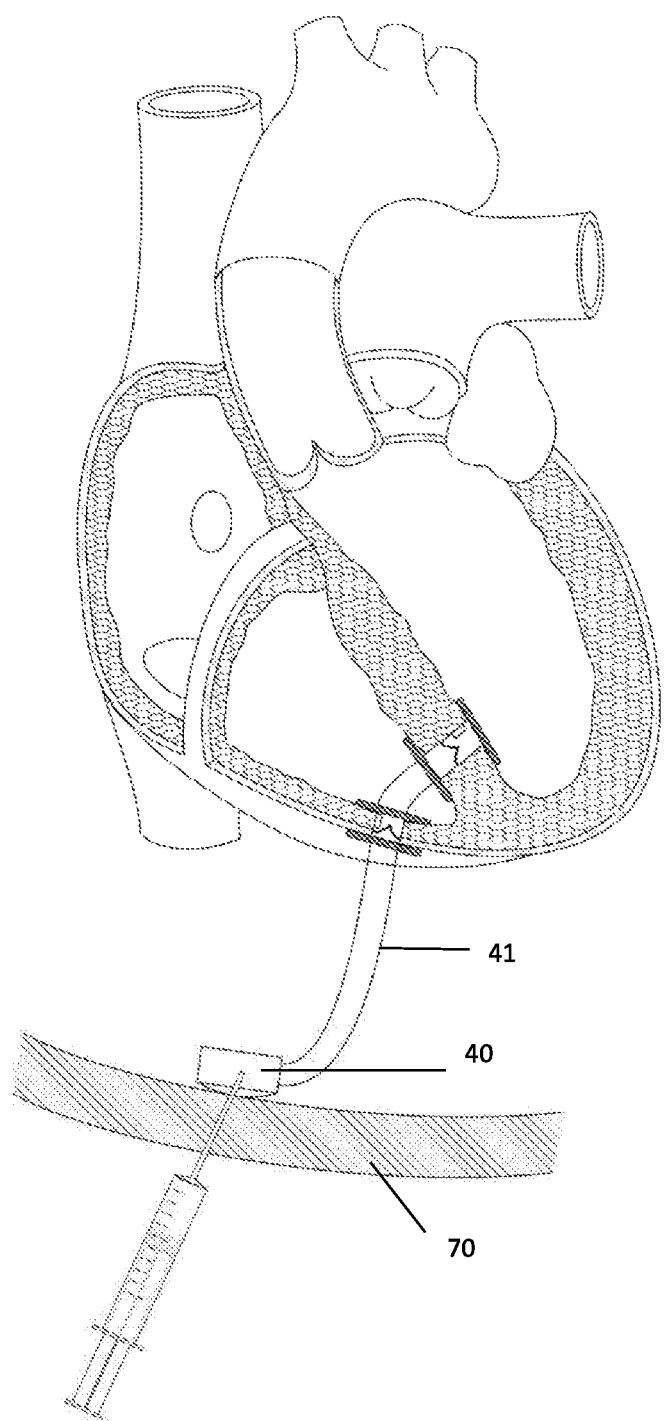

FIG. 10 shows a port device. The insertion unit according to the invention is connected with a port catheter (41) and thus creates a unit that allows gaining access to the left and right ventricle and to the abdominal cavity, if required. The subcutaneously implanted hollow chamber with silicone membrane (port chamber) (40) is connected with the insertion unit by a port catheter (41). The port chamber can be filled up through a membrane by means of an injection through the abdomen. A direct access to the ventricles is thus achieved by which medicine, contrast agents, blood thinners, stem cells etc. can be applied or blood samples can be withdrawn.

Figure 11:
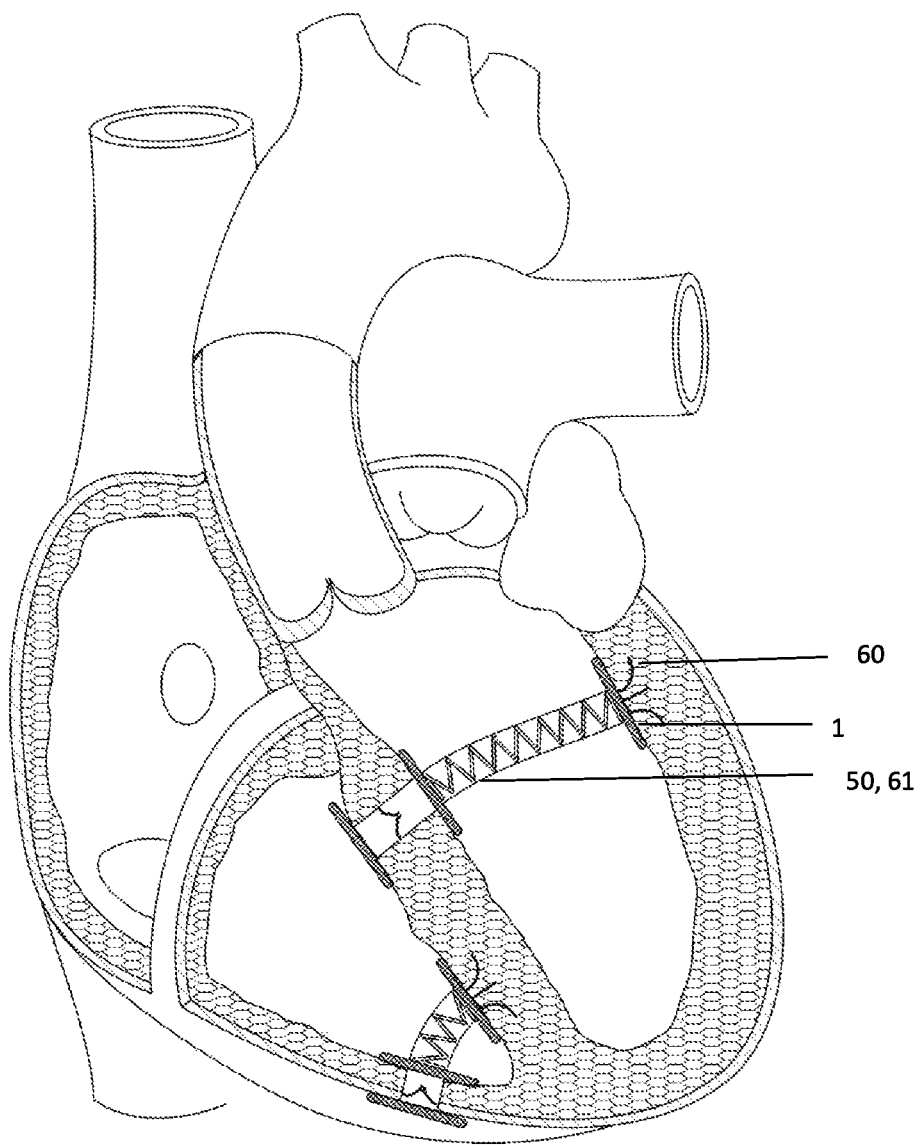

FIG. 11 shows a device for reducing the ventricle size in case of a pathological ventricle enlargement. The inventive insertion unit is modified by reducing the number of distally placed discs. There is only one distally placed disc (1) having fixation hooks (60) so that an unit is created that can be fixed in the heart muscle tissue resp. in the ventricular septum. The central section (50) is formed as a spring (61)

Figure 12:
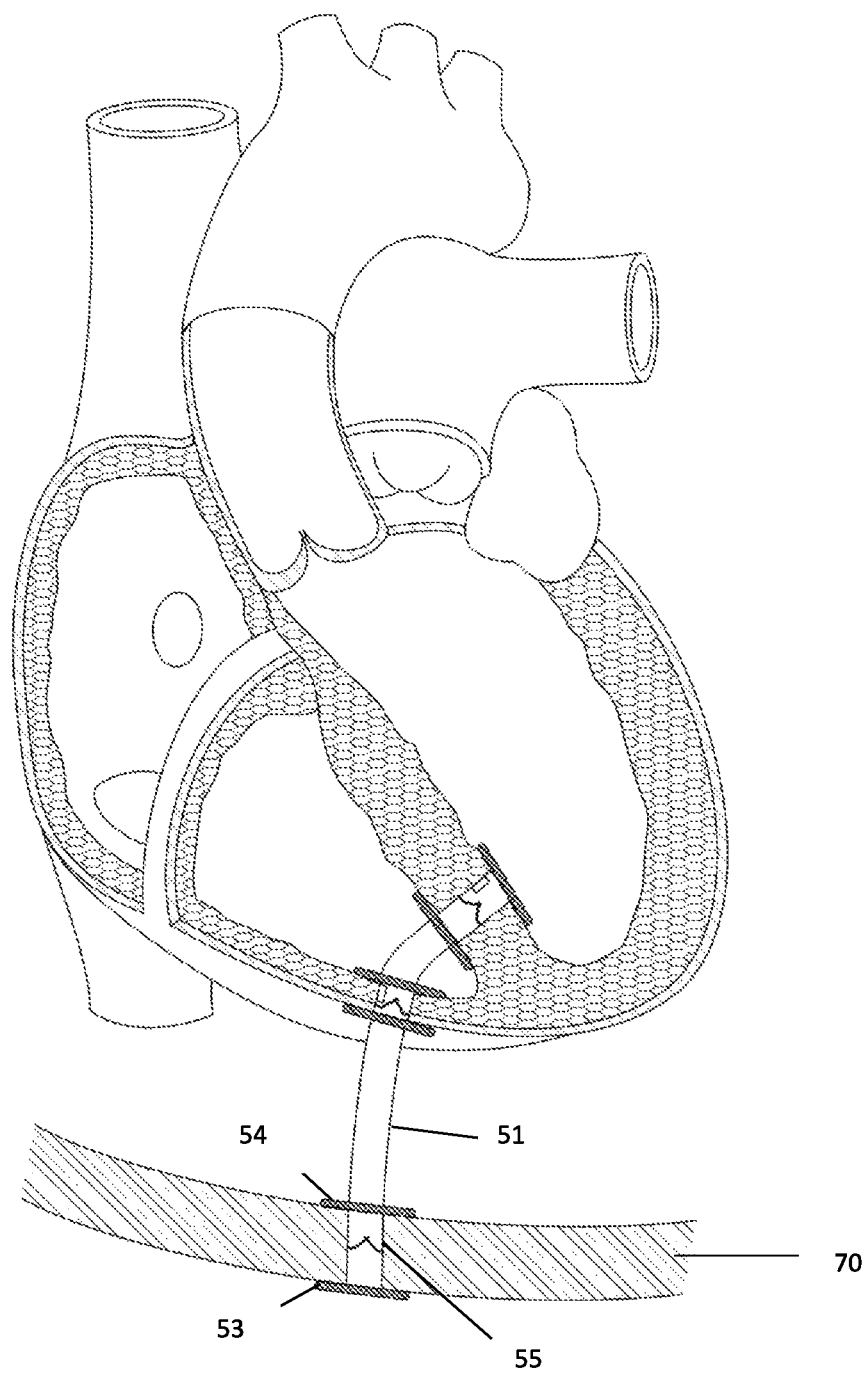

FIG. 12 shows the insertion unit implanted in the heart chambers, as shown in FIG. 2 for the access to the abdomen, right ventricle and left ventricle of the heart at any time. However, the tubular shaft (5) is longitudinally extended to form an extended shaft (51). Shaft (51) is guided through the chest wall (70) resp. through the abdominal wall. The extended shaft (51) comprises double disc (53), (54) with pressure valve (55) sealing the chest wall. Double disc (53), (54) is equivalent to double disc (1), (2) resp. (3), (4).

Figure 13:
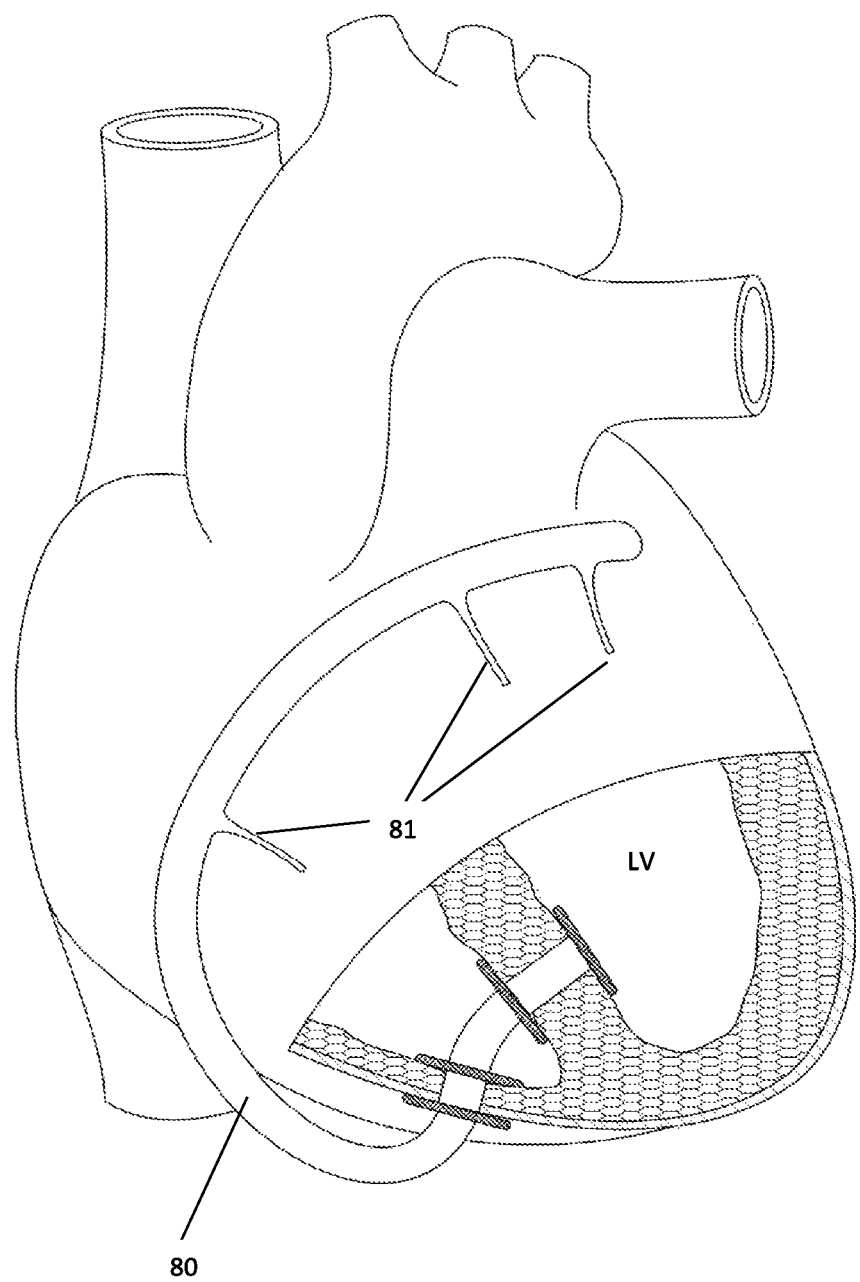

FIG. 13 shows a device for taking blood from the left ventricle and for supplying the heart muscle tissue with blood via the coronary arteries.

The insertion unit implanted in the heart chambers as shown in FIG. 2 is combined with an artificial blood vessel (80) being a tube. One end of the tube is placed and fixed within the shaft (5) of the insertion unit. Thus the artificial blood vessel (80) has direct access to the left ventricle (LV). The artificial vessel (80) is placed over the heart and fixed on the heart tissue above the ventricles. The artificial vessel has several small branches (81) serving as bypasses.

Figure 14:
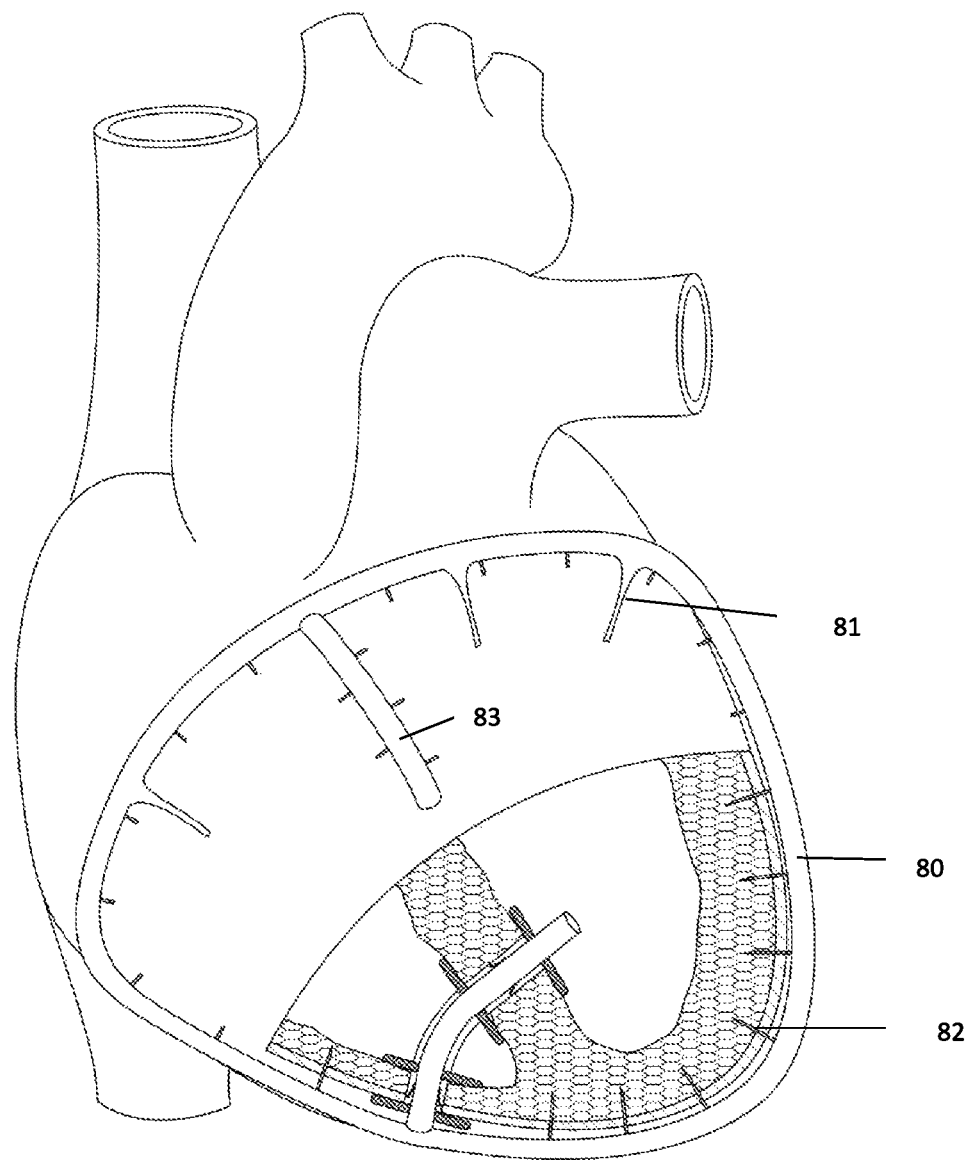

FIG. 14 also shows a device in which the insertion unit according to the invention is combined with an artificial blood vessel (80) (83) being a tube. Contrary to the device described in FIG. 13, the artificial blood vessel is arranged in a circle around the heart. The tubular body of the artificial blood vessel has small branches (81) serving as bypasses. Furthermore, cannula-like branches (82) are arranged along the circular vessel that extend up into the myocardium like an injection needle and supply the myocardium with more blood in order to initiate some new arteries.

Figure 15:
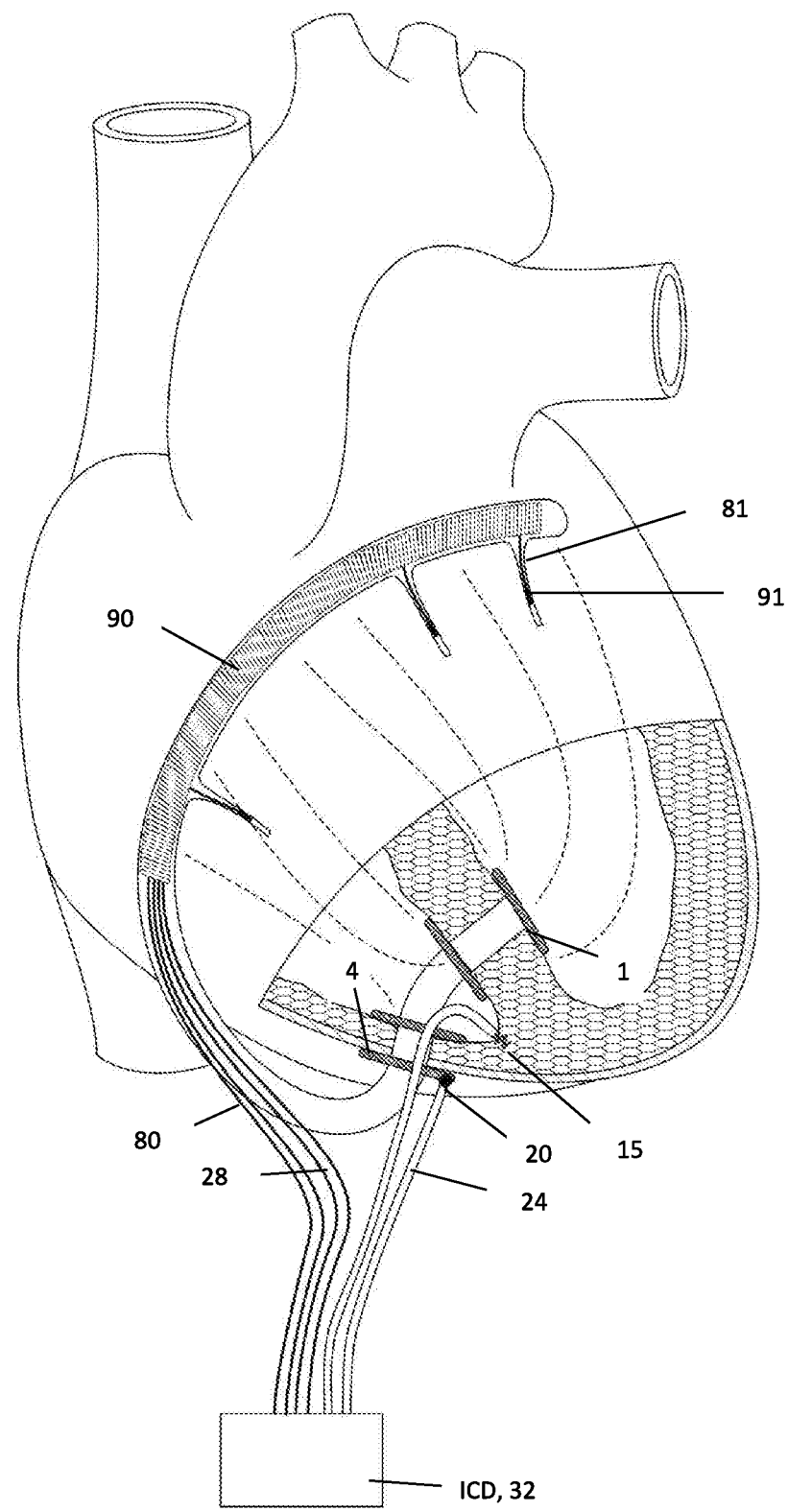

FIG. 15 shows a device for taking blood from the left ventricle, said device can simultaneously be used for the stimulation and defibrillation of the heart.

In addition to the device shown in FIG. 13 the tubular body of the artificial blood vessel (80) is wrapped in part with a metallic coil (90) to form an electrical defibrillation pole. The coil (90) is connected to an ICD via one of the electrical connection lines (28). If desired, the defibrillation shock is given between coil (90) and the insertion unit (20) The insertion unit is connected to the ICD via the electrical connection line (24) that leads to the proximally placed disc (4). The whole insertion unit (the discs 1,2,3,4) thus serves as second defibrillation electrode or as indifferent pole. Said second defibrillation electrode is equivalent to the defibrillation electrode described in FIGS. 8 and 9.

Further electrical connection lines (28) lead from the measurement device (32) to the small branches (81) and to the electrodes (91) placed around the branches (81). By measuring individually the electrical impedance between each of the electrodes (91) the blood flow in each bypass can be controlled. The detailed positioning of the control electrodes (sensors) is shown in FIG. 16.

The screw electrode (15), which is monitoring the ECG is connected to an ICD. In case of ventricular fibrillation the shock process starts. Analogue to the device shown in FIG. 8 a further screw electrode can be fixed in the left ventricle. FIG. 15 also shows the field strength distribution during the defibrillation. The positioning of the defibrillation electrodes results an optimal field strength distribution so that less shock energy is required.

Figure 16:
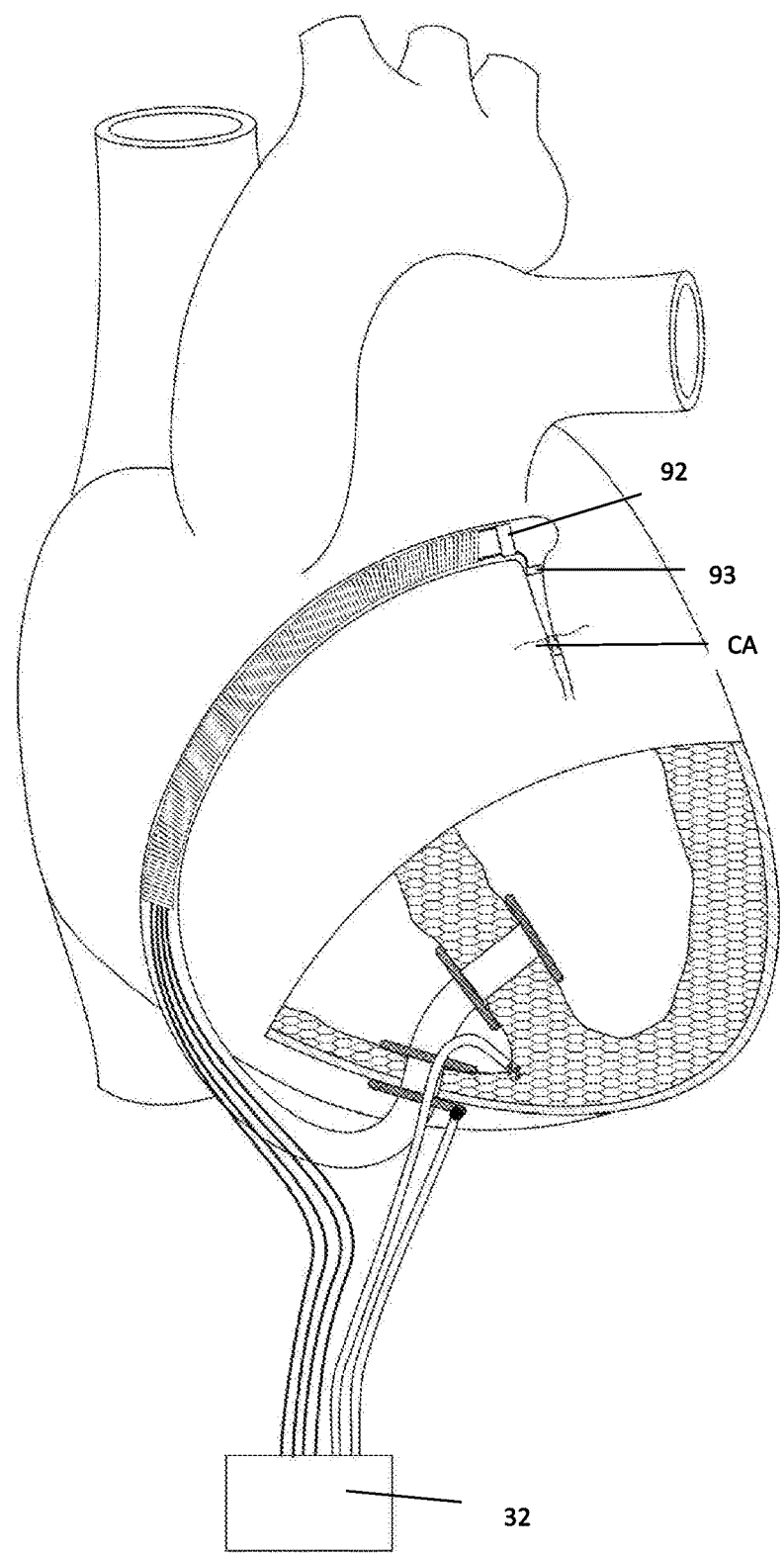

FIG. 16 shows a device for the bypass control. In addition to the device shown in FIG. 15, the positioning of the control electrodes/sensors is shown in detail. The control electrodes (91) consist of two electrodes (92, 93) spaced circularly around the artificial blood vessel and being in contact with an electrical impedance measurement unit (32). The electrodes (92), (93) are suitable to monitor the blood flow in the bridged coronary artery (CA, bypass).

Figure 17:
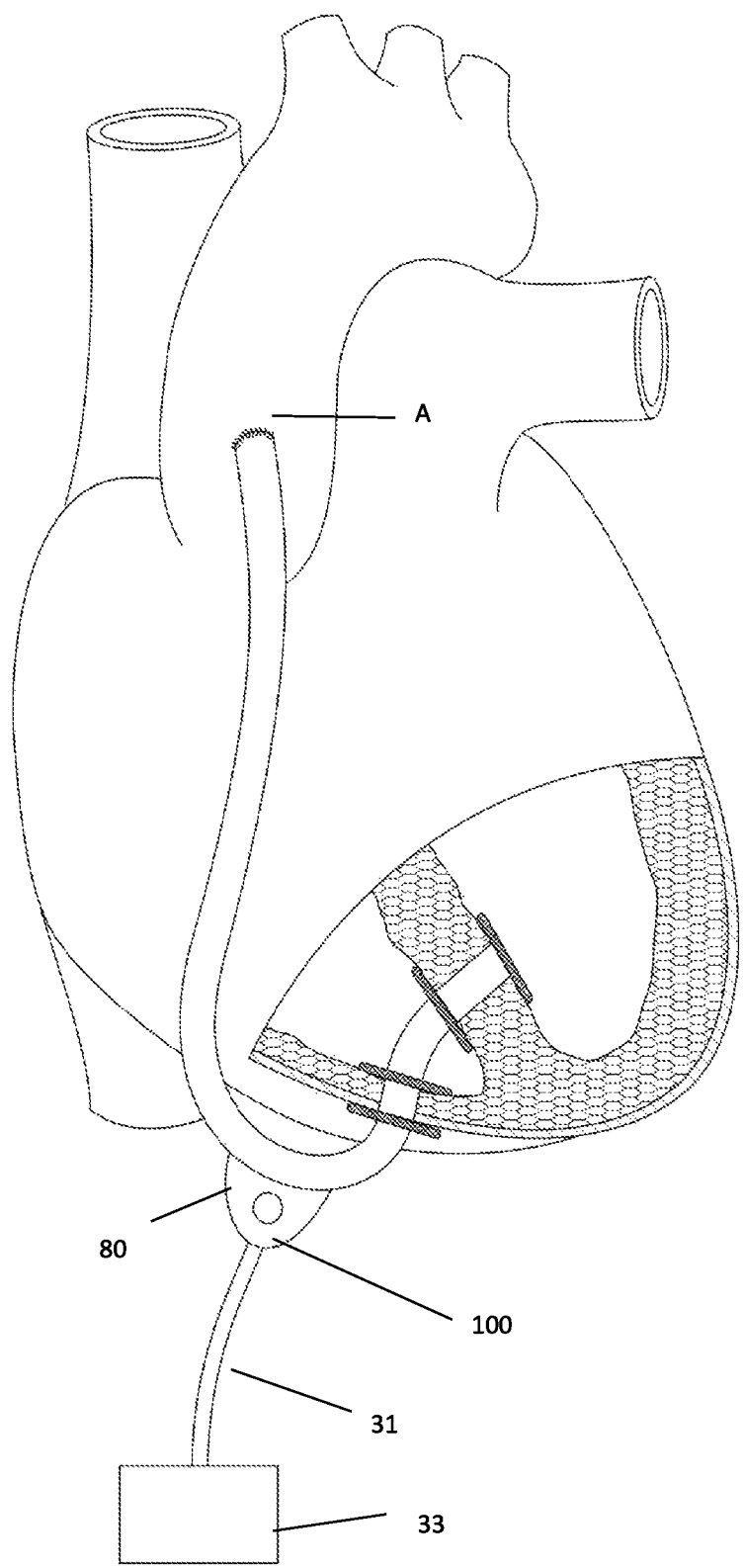

FIG. 17 shows a device for the support of the cardiac output. The inventive insertion unit is connected to an artificial blood vessel system consisting of a tube (80), one end of the tube being placed and fixed within the shaft of the insertion unit and the other end is configured to be disposed in the aorta (A). A blood pump (hose pump) (100) is placed into the tube (80). The hose pump sucks blood from the left ventricle and transports it into the aorta. The connection from the pump (100) to the control unit (33) is lead through the chest wall.

Figure 18:
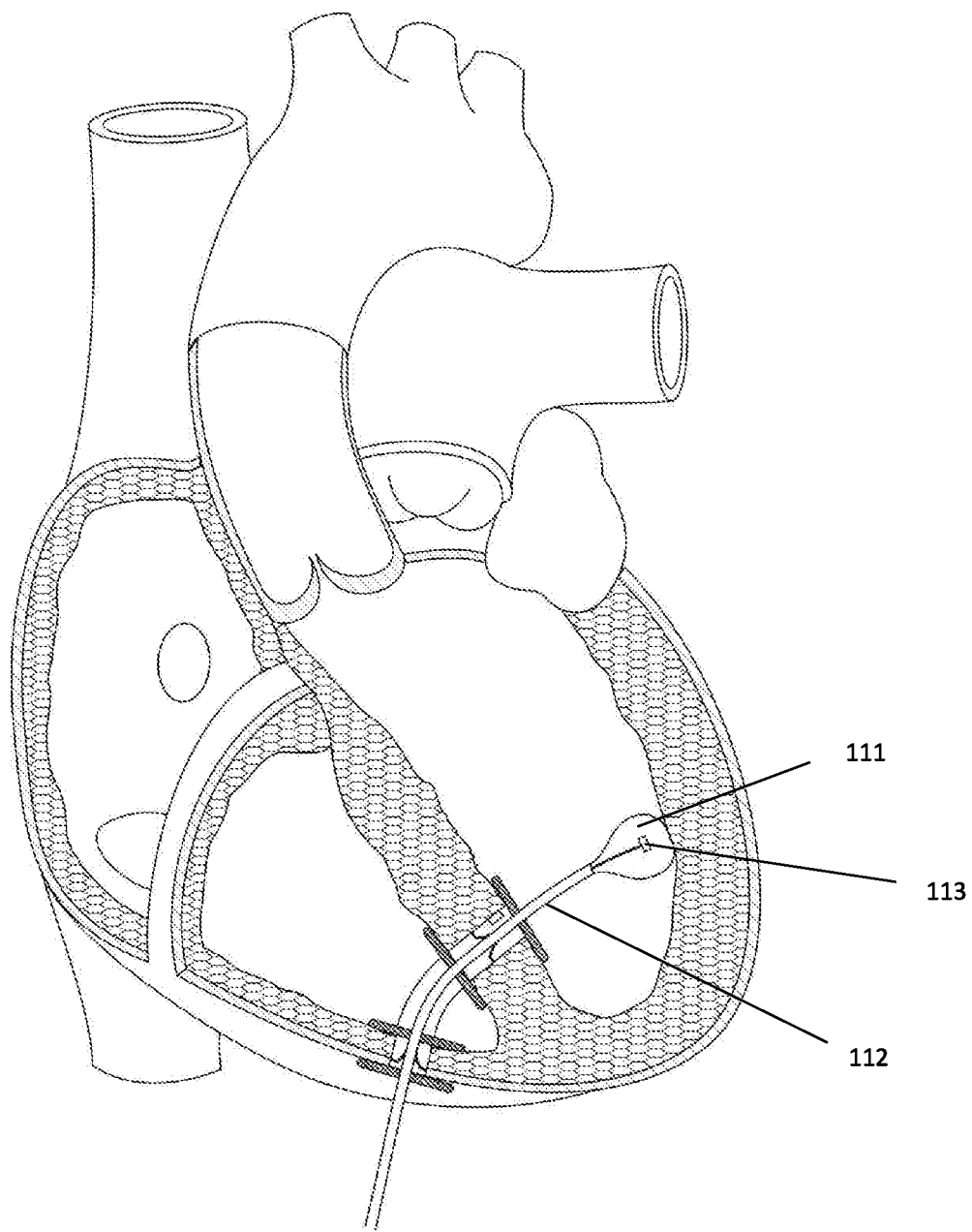

FIG. 18 shows a device for detecting and inspecting changes in the inner heart tissue. Catheter type endoscopes having a shaft (112) and a tip (113) with a video chip and a light fiber at the tip within a transparent balloon (111) can be inserted through the shaft of the inventive insertion unit and guided to the inner part of the heart. By inflating the transparent balloon with CO2 gas or saline solution and pushing it to the desired area, the endoscope can inspect visually structural defects in the interior parts of the heart and vessels.

Figure 19:
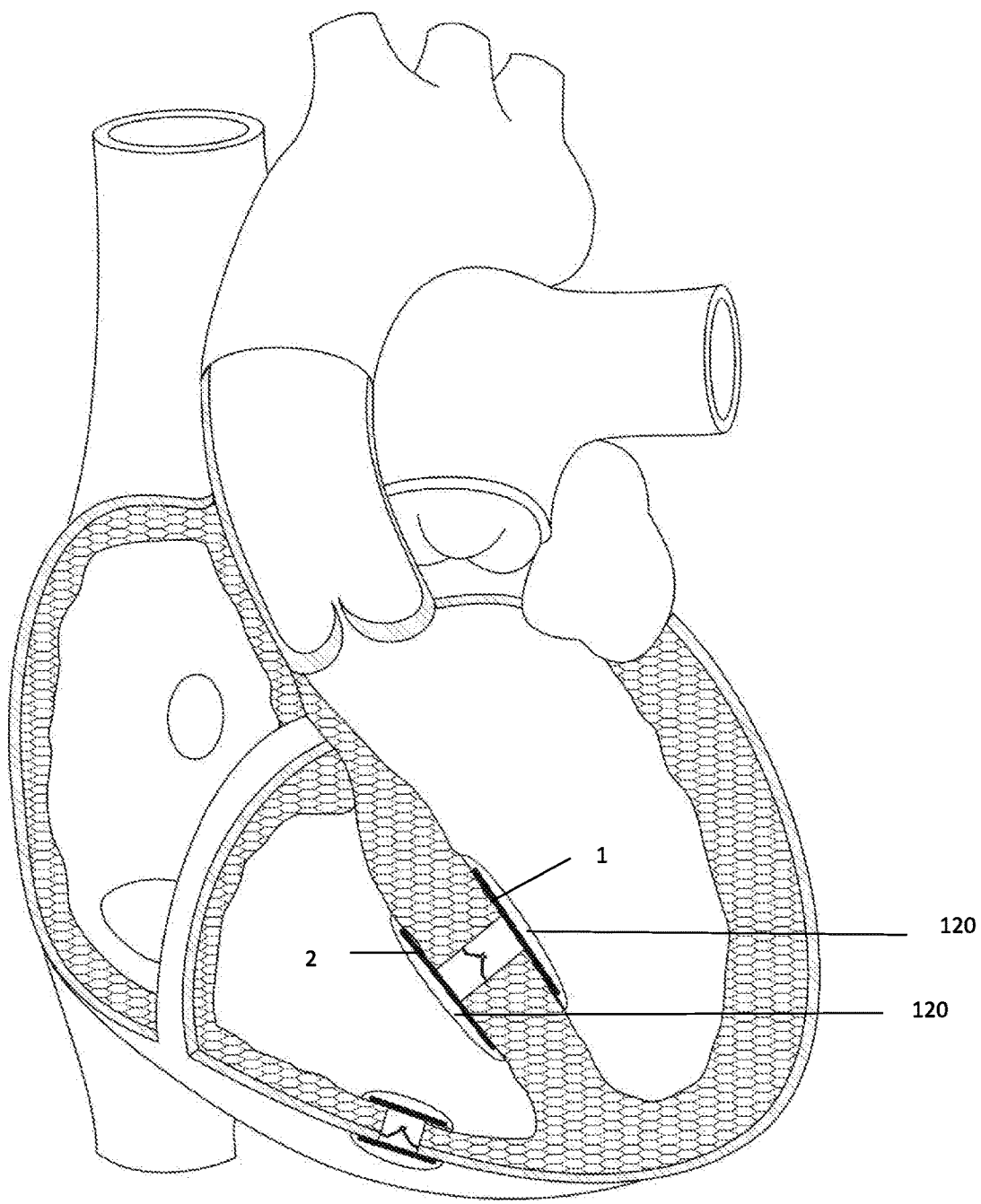

FIG. 19 shows a closing device using enlarged braided occlusion discs (1), (2) being equivalent to the braided discs (1), (2) as described in FIG. 2 as clamping means for closing ventricular septal defects (VSD) or rupture. The occlusion discs (1), (2) are covered with special tissue growing material (120).

Figure 20:
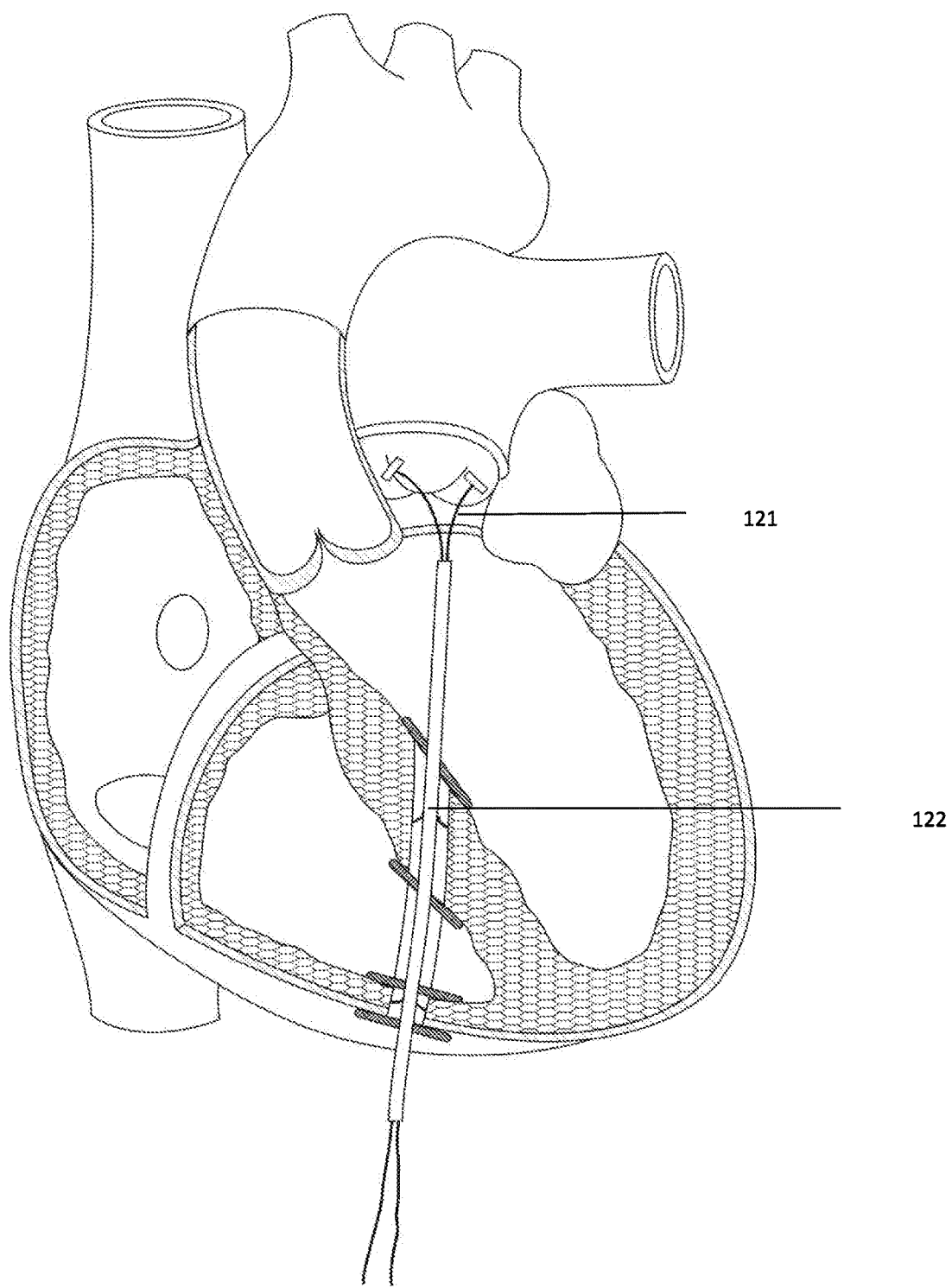

FIG. 20 shows a device for improving the mitral cardiac valve geometry by reducing the valve area.

A catheter (122) is inserted through the shaft of the inventive insertion unit. A device for pushing anchors (121) like T-bars with attached surgical sutures are pushed through said catheter and guided to the cardiac valve and knot together. A device for pushing suitable anchors is described in WO2007079952 corresponding to US20090012557.

Figure 21:
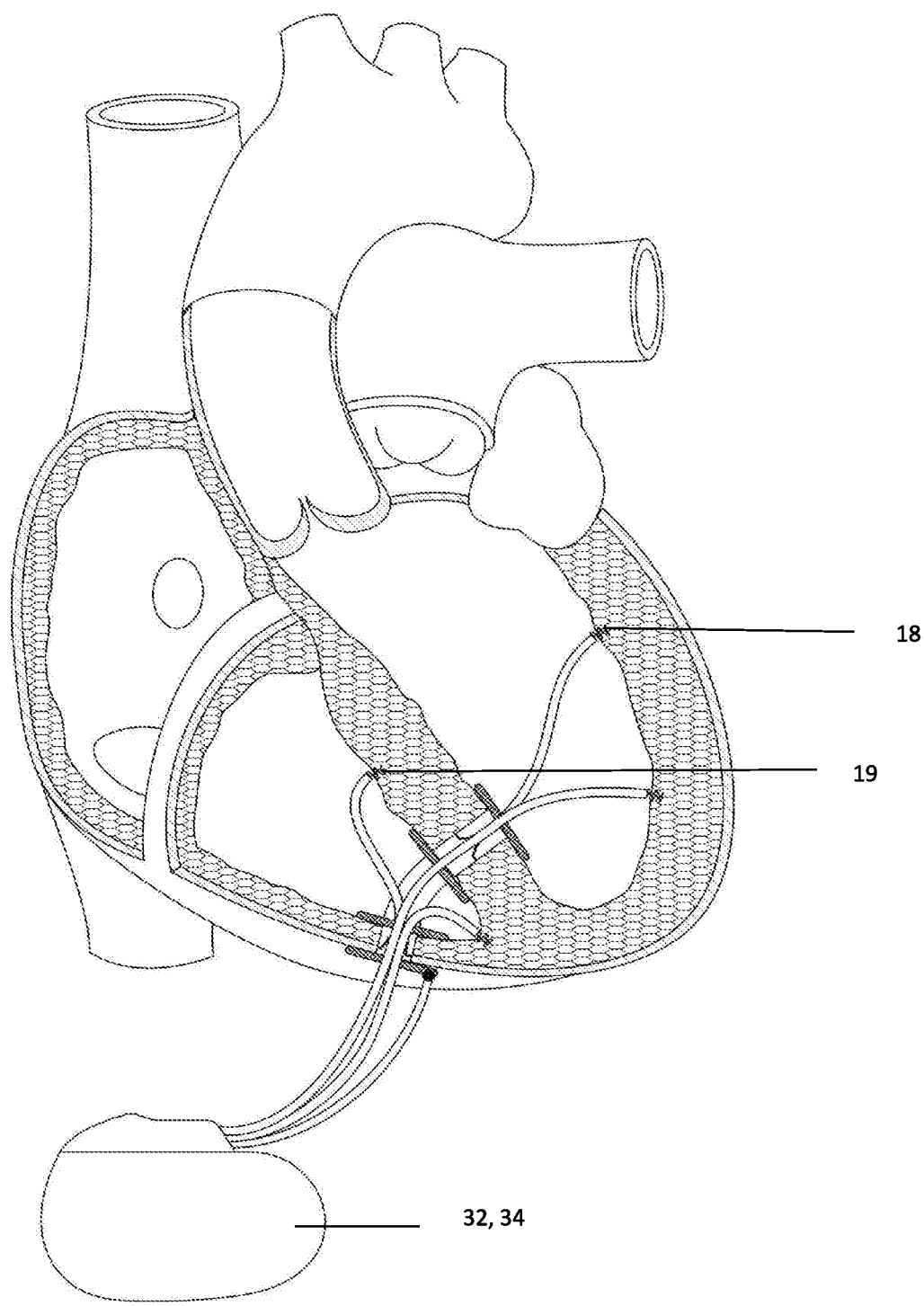

FIG. 21 shows a device for calculating and monitoring the cardiac output.

A first impedance measuring electrode (18) resp. (19) is inserted through the shaft of the insertion unit and fixed in the tissue of the left ventricle resp. the right ventricle. The electrode (18) in the left ventricle is one pole; the electrode (19) in the right ventricle is the other pole. Both poles are connected to an impedance measuring device (32) thus forming an impedance measurement circuit. The cardiac synchronous impedance change which is temporally concordant with the stroke volume is determined.

An apparatus and a method for determining an approximate value for the stroke volume and the cardiac output of a person's heart is described in U.S. Pat. No. 6,511,438.

FIG. 22 shows a device for the cardiac valve replacement and/or the dilation of the replaced valves.

FIG. 22a shows the device implanted in the heart. Similar to the device shown in FIGS. 3 and 4 a catheter (trocar) (10) is inserted through shaft (5) of the inventive insertion unit and guided to the left ventricle. Cardiac valve prosthesis mounted on metal frame (11) said frame being positioned on a dilatation catheter (133) is pushed through said trocar (10) and guided to the aortic valve to be replaced. The dilation catheter (133) comprises elongated expanding formed metal elements (131), preferably made from Nitinol or stainless steel.

FIG. 22b shows the basket designed dilatation catheter in folded and unfolded position. The basket is expanded by using a handle actuation (133) by turning the handle. The turn mechanism enables precise adjusting of the diameter of the basket, which is especially important for post dilatation purposes, reducing any leakage problems. The advantage compared to the balloon catheter is, that during the procedure the blood can continue to flow.

The invention claimed is:

1. Device for stimulation and/or defibrillation, comprising:
    an insertion unit including a tubular shaft with a lumen extending there through, said shaft having distal, proximal and central sections, whereby the distal and proximal sections of the shaft are disc-shaped when extended, thus forming each a double disc, whereby the central section of the shaft links the distally placed double disc with the proximally placed double disc, and whereby a pressure valve is fixed inside the shaft on both the distal and proximal end sections thereof respectively; and
    at least one stimulation electrode connected to a pacemaker, each electrode including a lead provided with a pole at a distal end thereof, whereby the insertion unit is conductive and is connected to an implantable cardiac defibrillator to form one of a defibrillation electrodes or to form an indifferent pole and whereby the lead of the stimulation electrode runs inside the shaft of the insertion unit.

2. Device according to claim 1, wherein the insertion unit consists of braided wires of memory material.

3. Device according to claim 1, wherein the insertion unit consists in part or in total of Silicon, Polyurethane, PTFE, Polyester, biocompatible fibers, Nitinol, Titanium or Stainless Steel.

4. Device according to claim 1, whereby an inner and/or an outer portion of the central section of the tubular shaft of the insertion unit is covered by a biocompatible synthetic material.

5. Device according to claim 1, whereby the central section of the tubular shaft of the insertion unit is coil shaped.

6. Device according to claim 1, whereby the tubular shaft of the insertion unit is longitudinally extended thus forming an extended shaft, the thus extended shaft comprising a further double disc with pressure valve at its proximal end.

7. Device according to claim 1, whereby the distal section of the shaft has only one disc having fixation hooks and whereby the central section of the tubular shaft is elastic.

8. Device according to claim 1, whereby the proximally placed disc of the double disc is connected to a port chamber by a port catheter.

\* \* \* \* \*